US012268705B2

(12) United States Patent
Sugita et al.

(10) Patent No.: US 12,268,705 B2
(45) Date of Patent: *Apr. 8, 2025

(54) USE OF POLYSACCHARIDE FOR TREATING ST-ELEVATION MYOCARDIAL INFARCTION AND DISEASES OF THE DIGESTION SYSTEM

(71) Applicant: PT. Sahabat Lingkungan Hidup, Surabaya (ID)

(72) Inventors: Peter Sugita, Surabaya (ID); Wiwiek Widyastuti Budiliantono, Surabaya (ID); Aurelia Maxine Sugita, Surabaya (ID)

(73) Assignee: PT. SAHABAT LINGKUNGAN HIDUP, Surabaya (ID)

( * ) Notice: Subject to any disclaimer, the term of this patent is extended or adjusted under 35 U.S.C. 154(b) by 0 days.

This patent is subject to a terminal disclaimer.

(21) Appl. No.: 18/232,135

(22) Filed: Aug. 9, 2023

(65) Prior Publication Data

US 2024/0216417 A1 Jul. 4, 2024

Related U.S. Application Data

(63) Continuation of application No. 17/194,916, filed on Mar. 8, 2021, now Pat. No. 11,766,450, which is a continuation of application No. 15/806,048, filed on Nov. 7, 2017, now Pat. No. 10,940,162.

(60) Provisional application No. 62/553,647, filed on Sep. 1, 2017, provisional application No. 62/419,174, filed on Nov. 8, 2016.

(51) Int. Cl.
| A61K 31/716 | (2006.01) |
| A61K 36/074 | (2006.01) |
| A61P 1/00 | (2006.01) |
| A61P 1/04 | (2006.01) |
| A61P 9/10 | (2006.01) |
| A61P 29/00 | (2006.01) |

(52) U.S. Cl.
CPC .......... *A61K 31/716* (2013.01); *A61K 36/074* (2013.01); *A61P 1/00* (2018.01); *A61P 1/04* (2018.01); *A61P 9/10* (2018.01); *A61P 29/00* (2018.01)

(58) Field of Classification Search
CPC ....... A61K 31/716; A61K 36/074; A61P 9/10; A61P 1/00; A61P 29/00; A61P 1/04
USPC .......................................................... 514/54
See application file for complete search history.

(56) References Cited

U.S. PATENT DOCUMENTS

| 6,893,641 | B2 | 5/2005 | Chung et al. |
| 7,135,183 | B1 | 11/2006 | Wang et al. |
| 10,940,162 | B2* | 3/2021 | Sugita ............... A61P 29/00 |
| 11,766,450 | B2 | 9/2023 | Sugita et al. |
| 2003/0143246 | A1 | 7/2003 | Chung et al. |
| 2018/0125879 | A1 | 5/2018 | Sugita et al. |
| 2021/0187009 | A1 | 6/2021 | Sugita et al. |

FOREIGN PATENT DOCUMENTS

| WO | WO 2005/084692 | 9/2005 |
| WO | WO 2009/063221 | 5/2009 |

OTHER PUBLICATIONS

Feiffel JA. Practical Algorithms for Pharmacologic Management of the Post Myocardial Infarction Patient. Clin. Cardiol. vol. 28 (Suppl. I), 1-28-1-37 (2005) (Year: 2005).*
"The effects of GLPP (Ganoderma lucidum polysaccharide peptide) to decrease chronic inflammation and oxidative stress marker in atherogenesis and diabetes mellitus," Abstract Collection, 2014, 25 pages.
[No author listed], "Cardiac Surgery in Pennsylvania: Information about hospitals and cariothoraic surgeons," Pennsylvania Health Care Cost Containment Council, Jun. 2007, 40 pages.
[No Author Listed], "Case Report: The Use of PsP as Complementary Therapy in Cardiovascular Diseases," PT. Sahabat Lingkungan Hidup, Jan. 2016, Document No. SPS/04/CR-PsPCVD/ SLH/0116/ REVE, 29 pages.
[No Author Listed], "Case Report: The Use of Sharko and PsP as Complementary Therapy in Cancer," PT. Sahabat Lingkungan Hidup PT, Jan. 2016, Document No. SPS/17/CR-SC-PsPCa/ SLH/0116/ REV E, 21 pages.
[No Author Listed], "Case Study the Use of PsP as Complementary Therapy in Idiopathic Thrombocytopeniarpura, " PT. Sahabat Lingkungan Hidup, Feb. 2009, 8 pages.
[No author listed], "Mushroom identification certificate of Ganoderma lucidum from: 1. Center for International Services to Mushroom Biotechnology 2. Indonesian Institute of Sciences, Research Center for Biology," Research Center for Biology, Jan. 23, 2015, 2 pages.
[No author listed], "Product Monograph: Psp (Ganoderma lucidum Polysaccharide Peptide) Immunomodulator," SLH Labs, 2017, 52 pages.
[No author listed], "PsP (Ganoderma lucidum Polysaccharide Peptide) Draft Monograph," SLH Labs, 2013, 25 pages.
[No author listed], "PsP (Ganoderma lucidum Polysaccharide Peptide) Draft Monograph," SLH Labs, Jan. 2011, 2 pages.
[No author listed], "PsP (Ganoderma lucidum Polysaccharide Peptide) Draft Monograph," SLH Labs, Jan. 2013, 2 pages.
Aarsaether et al., "Cardioprotective effect of pretreatment with b-glucan in coronary artery bypass grafting," Scandinavian Cardiovascular Journal, 2006, 40:298-304.
Aarsaether et al., "Oral β-glucan reduces infarction size and improves regional contractile function in a porcine ischaemia/reperfusion model, " European Journal of Cardio-Thoracic Surgery, Apr. 2012, 41(4):919-925.

(Continued)

*Primary Examiner* — Yih-Horng Shiao
(74) *Attorney, Agent, or Firm* — Fish & Richardson P.C.

(57) ABSTRACT

Provided herein are methods of treating ST-elevation myocardial infarction (STEMI) and diseases of the digestion system using β-1,3/1,6-D-glucan derived from mycelium extract of *Ganoderma lucidum*. Methods of treating ST-elevation myocardial infarction (STEMI) and diseases of the digestion system using a polysaccharide comprising β-1,3/ 1,6-D-glucan are also provided.

25 Claims, 18 Drawing Sheets

(56) References Cited

OTHER PUBLICATIONS

Akramiene et al., "Effects of β-glucans on the immune system," Medicina, 2007, 43(8):597-605.
Alwi et al., "Infrak miokard akut dengan elevasi st / Acute Infarc Miokard with ST elevation," Internal Medicine, 2014, vol. II, ed. VI, Ch. 191; pp. 1459-1460.
Arora et al., "Treatment response evaluation and follow-up in hepatocellular carcinoma," Journal of Clinical and Experimental Hepatology, 2014, 4(53):S126-S129.
Balatbat, "Glycated (Glycosylated) Hemoglobin: HbA1c New directions to diagnose diabetes," Continuing Education Topics & Issues, 2010 Article 368, 112-115.
Berdal, "Aminated β-1,3-D-Glucan improves wound healing in diabetic db/db mice," Wound Repair and Regeneration, 2007, 15(6):825-832.
Boos et al., "Circulating Endothelial Cells in Cardiovascular Disease," J Am Coll Cardiol., 2006, 48 (8):1538-1547.
Brashers, "Pathophysiology: The Biologic Basis for Disease in Adults and Children, Chapter 30: Alterations of Cardiovascular Function," Elsevier Mosby, 2006, 1081-1146.
Cao et al., "Antitumor and Antiangiogenic Activity of Ganoderma lucidum Polysaccharides Peptide," Acta Pharmacol. Sin., 2004, 25(6):833-838.
Cao et al., "Ganoderma lucidum Polysaccharides Peptide Inhibits the Growth of Vascular Endothelial Cell and the Induction of VEGF in Human Lung Cancer Cell," Life Sciences, 2006, 78:1457-1463.
Case Report, "The use of PsP as a complementary therapy in patients with cardiovascular diseases," PT Sahabat Lingkungan Hidup Biopharmaceutical Company, 2015, 29 pages.
Cerci et al., "The Effects of Topical and Systemic Beta Glucan Administration on Wound Healing Impaired by Corticosteroids," HTU, 2008, http://www.woundsresearch.com, 8 pages.
Chan et al., "Ganoderma lucidum mycelium and spore extracts as natural adjuvants for immunotherapy," J. Altern Complement Med., 2005, 11(6):1047-57.
Chan et al., "The effects of B-glucan on human immune and cancer cells," Journal of Hematology & Oncology, 2009, 2(25):1-11.
Chen et al., "Effects of Ganoderma lucidum and Krestin on subset T-cell in Spleen of γ-irradiated Mice," American Journal of Chinese Medicine, 1995, 23(3-4): 289-298.
Chu et al., "Study of potential cardioprotective effects of Ganoderma lucidum (Lingzhi): results of a controlled human intervention trial," British Journal of Nutrition, 2012, 107:1017-1027.
Cines et al., "Immune Thrombocytopenia Purpura," N Engl J Med., 2002, 346(13):995-1008.
Clark et al., "Biology and Chemistry of B-Glucan: Beta Glucans, Mechanisms of Action," Bentham Science Publishers, 2011, 1: 19-38.
Cleary et al., "The Effect of Molecular Weight and β-1,6-linkage on Priming of Macrophage Function in Mice by (1,3)-β-D-Glucan," Immunology and Cell Biology, 1999, 77:395-403.
Daba et al., "Anti-cancer effect of polysaccharides isolated from higher basidiomycetes mushrooms," African Journal of Biotechnology, 2003, 2(12): 672-678.
Danese et al., "Ulcerative Colitis," N. Engl. J. Med., 2011, 365-1713-25.
Davis, "Atherosclerosis—An Inflammatory Process," Journal of Insurance Medicine, 2005, 37:72-75.
Dinc et al., "Effects of Beta-D-glucan on Steroid-induced Impairment of Colonic Anastomotic Healing," Acta Chirurgica Belgica, 2006, 106:63-67.
Dolan et al., "The Sepsis syndrome," Health Research Cancer Care, 2000, 54-57.
Duque et al., "Macrophage Cytokines: Involvement in Immunity and Infectious Disease,". Frontiers in Immunology, 2014, 5(491):1-13.
Falanga, "Wound Healing and Its Impairment in the Diabetic Foot," Lancet, 366(9498):1736-43, (Nov. 12, 2005).
Foey et al., "Regulation of Monocyte IL-10 Synthesis by Endogenous IL-1 and TNF-α: Role of the p38 and p24/44 Mitogen-Activated Protein Kinases," The Journal of Immunology, 1998, 160: 920-928.
Fukai et al., "Superoxide Dismutases: Role in Redox Signaling, Vascular Function and Diseases," Antioxidants & Redox Signaling, 2011, 15(6):1583-1606.
Gao et al., "A Phase I/II Study of a Ganoderma lucidum (Curt.: Fr.) P. Karst (Ling Zhi, Reishi Mushroom) Extract in Patients with Chronic Hepatitis B," International Journal of Medicinal Mushrooms, 2002, 4:321-327.
Gao et al., "A phase I/II Study of a Ganoderma lucidum (Curt.: Fr.) P. Karst. Extract (Ganopoly) in Patients with Advanced Cancer," International Journal of Medical Mushrooms, 2002, 4:207-214.
Gao et al., "A Phase I/II Study of Ling Zhi Mushroom Ganoderma lucidum (W.Curt.: Fr.)Lloyd (Aphyllophoromycetideae) Extract in Patients with Type II Diabetes Mellitus," International Journal of Medical Mushrooms, 2004, 6:33-39.
Gao et al., "A phase I/II study of ling zhi mushroom Ganoderma lucidum (W.Curt.:FR) lloyd (aphyllophoromycetideae) extracts in patients with coronary heart disease," International Journal of Medicinal Mushrooms, 2004, 6:327-334.
Gao et al., "Antibacterial and Antiviral Value of the Genus Ganoderma P. Karst Species (Aphyllophoromycetideae): A Review," International Journal of Medicinal Mushrooms, 2003, 5:235-246.
Gao et al., "Effects of Ganopoly (A Ganoderma lucidum Polysaccharide Extract) on the Immune Functions in Advanced-Stage Cancer Patients," Immunological Investigations, 2003, 32(3): 201-215.
Gao et al., "Hepatoprotective Activity and the Mechanisms of Action of Ganoderma lucidum (Curt.:Fr.) P. Karst. (Ling Zhi, Reishi Mushroom) (Aphyllophoromycetideae) (Review)," International Journal of Medical Mushrooms, 2003, 5:111-131.
Gao et al., "Randomized, Placebo-Controlled, Multicenter Study of Ganoderma lucidum (W.Curt.:Fr.) Lloyd (Aphyllophoromycetidae) Polysaccharides (Ganopoly) in patients with Advanced Lung Cancer," International Journal of Medicinal Mushrooms, 2003, 5:369-381.
Gradinaru et al., "Oxidized LDL and NO synthesis—Biomarkers of endothelial dysfunction and ageing," Mechanisms of Ageing and Development, Nov. 2015, 151:101-113.
Gu et al., "Role of coronary artery bypass grafting during the acute and subacute phase of ST-elevation myocardial infarction," Neth. Heart J., 2010, 18:348-354.
Gustafson et al., "Inflammation and Impaired Adipogenesis in Hypertrophic Obesity in Man," Journal on Endocrinal Metab., 2009, 297:E999-E1003.
Hanaoka et al., "The Water-Soluble Extract from Cultured Medium of Ganoderma lucidum (Reishi) Mycelia (Designated as MAK) Ameliorates Murine Colitis Induced by Trinitrobenzene Sulphonic Acid," Scandinavian Journal of Immunology, 2011, 74:454-462.
Handayani et al., "LBPS 01-05: Ganoderma lucidum polysaccharide peptides as antioxidant, anti-inflammation, anti-hypertension and anti-lipid in high-risk patients of atherosclerosis," Journal of Hypertension, 2016, 34:e175.
Handayani et al., "PS 16-11: Ganoderma lucidum polysaccharide peptides: a potent protective endothelial vascular and anti-lipid in atherosclerosis," Journal of Hypertension, 2016, 34:e468.
Handayani et al., "The development model of Ganoderma lucidum polysaccharide peptides as antioxidant and anti-inflammation in patient with atherosclerosis," Presented at Annual Scientific Metting of Indonesian Heart Association, Jakarta, Indonesia, Apr. 15-17, 2016, 1 page.
Heiss et al., "The structure of Cryptococcus neoformans galactoxylomannan contains beta-D-glucuronic acid," Carbohydr. Res. 2009, 344(7):915-920.
Hendrawan et al., "The effect of polysaccharide peptide (ganoderma lucidum) on the decrease of chronic inflammation and oxidative stress markers in diabetes mellitus rat," Brawijaya Univeristy, 2013, 69 pages.
Heriansyah et al., "Reduction of histopathological images through a decrease in H202 levels in diabetic rats with polysaccharide peptides," Biomarkers and Genomic Medicine, 2015, 7:31-37.

(56) References Cited

OTHER PUBLICATIONS

Hermawan et al., "Polysaccharide peptide: a novel anti-inflammation in reducing intima media proliferation in diabetic rats," Indian Journal of Medical Research and Pharmaceutical Sciences, 2015, 2(12):29-35.
Hermawan et al., "Reduction of inflammation marker and histopathology changes by polysaccharide peptide (Gandermalucidum) in diabetic rats: protection in atherogenesis," Journal of Hypertension, 2015, 1 page, abstract only.
Hidup, "PsP B-1,3/1,6-D-Glucan from Ganoderma lucidum mycelia extract," Poster presentation, SLH labs, 2016, 25 pages.
Ho et al., "Biological markers of oxidative stress: Applications to cardiovascular research and practice," Redox Biology, 2013, 1:483-491.
Ho et al., "The safety of levofloxacin in tuberculosis treatment including drug-induced hepatotoxicity," Review, 2011, 25-31.
Hotchkiss et al., "Deletion of dendritic cells, but not macrophages, in patients with sepsis," J. Immunol., 2002, 168-2493-2500.
Hotchkiss et al., "Sepsis-induced apoptosis causes progressive profound depletion of B and CD4+T lymphocytes in humans," J. Immunol., 2001, 166:6952-6963.
Hotchkiss et al., "The pathophysiology and treatment of sepsis," The New England Journal of Medicine, 2003, 38(2):138-150.
Hristov et al., "Endothelial Progenitor Cells Mobilization, Differentiation, and Homing," Arterioscler. Thromb. Vasc. Biol., 2003, 23:1185-1189.
Hsu et al., "Extract of Reishi Polysaccharides Induces Cytokine Expression via TLR4-Modulated Protein Kinase Signaling Pathways," The Journal of Immunology, 2004, 173:5989-5999.
Hsu et al., "Polysaccharide purified from Ganoderma lucidum inhibits spontaneous and Fas-mediated apoptosis in human neutrophils through activation of the phosphatidylinositol 3 kinase/ Akt signaling pathway," J. Leukoc. Biol., 2002, 72: 207-216.
Hua et al., "Ganoderma lucidum polysaccharides enhance CD14 endocytosis of LPS and promote TLR4 signal transduction of cytokine expression," Journal of Cellular Physiology, 2007, 212:537-550.
Jia et al., "Evaluation of in vivo antioxidant activities of Ganoderma lucidum polysaccharides in STZ-diabetic rats," Food Chemistry, 2008, 115:32-36.
Jin-Zhe et al., "Analysis of Structural Characteristics of Polysaccharide from Ganoderma lucidum," Chinese Journal of Analytical Chemistry, 2010, 372-376 (with English abstract).
Jong et al., "Medicinal Benefits of the Mushroom Ganoderma," Advance in Applied Microbiology, 1992, 37:101-134.
Kalogeris et al., "Cell Biology of Ischemia/Reperfusion Injury," Int Rev Cell Molecular Biology, 2012, 298:229-317.
Kino et al., "Isolation and Characterization of a New Immunomodulatory Protein, Ling Zhi-8 (LZ-8), from Ganoderma lucidum," The Journal of Biological Chemistry, 1989, 264:472-478.
Kirk et al., "Dictionary of the Fungi," CABI Europe, 2008, 84 pages.
Kleinsmith et al., "Understanding Cancer and Related Topics: Understanding Cancer," National Cancer Institute, 2004, 63 pages, accessed at http://cancer.gov/cancertopics/understandingcancer.
Kougias et al., "Normal Human Fibroblast Express Pattern Recognition Receptors for Fungal (1®3)-β-D-Glucans," Infection and Immunity, 2001, 69(6):3933-3938.
Leksono et al., "Anti-inflammation effect of polysaccharide peptide (gandermalucidum) in diabetes mellitus," Journal of Hypertension, 2015, 1 page, abstract only.
Li et al., "Modulating Toll-Like Receptor Mediated Signaling by (1-3)-β-D-Glucan Rapidly Induces Cardioprotection," Cardiovascular Research, 2004, 61:538-547.
Li et al., "Reversal Effect of Ganoderma lucidum Polysaccharide on Multidrug Resistance in K562/ADM Cell Line," Acta Pharmacologica Sinica, 2008, 29(5):620-627.
Lieu et al., "The Effect of Ganoderma lucidum on Induction of Differential in Leukemic U937 Cells," Anticancer Research, 1992, 12:1211-1216.

Lin et al., "Polysaccharide purified from Ganoderma lucidum induced activation and maturation of human monocyte-derived dendritic cells by the NF-κB and p38 mitogen-activated protein kinase pathways," Journal of Leukocyte Biology, 2005, 78:533-543.
Lin, "Cellular and molecular mechanisms of immuno-modulation by Ganoderma lucidum," J Pharmacol. Sci., 2005, 99:144-153.
Lucas et al., "Atherosclerosis: Role of Chemokines and Macrophages," Expert Reviews in Molecular Medicine, 2001, 3(25):1-18.
Lull et al., "Antiinflammatory and immunomodulating properties of fungal metabolites," Mediators of Inflammation, 2005, 2:263-80.
Mahargo et al., "Antioxidant effect of polysaccharide peptide of Ganoderma lucidum in diabetic rats," Journal of Hypertension, 2015, 1 page, abstract only.
Maruyama et al., "Decreased Macrophage Number and Activation Lead to Reduce Lymphatic Vessel Formation and Contribute to Impaired Diabetic Wound Healing," The American Journal of Pathology, 2007, 170:1178-1191.
Molleken et al., "A new colorimetric method to quantify B-1,3-1,6-glucans in comparison with total B-1,3-glucans and a method to quantify chitin in edible mushrooms," Proceedings of the 7th International Conference on Mushroom Biology and Mushroom Products, 2011, 263-273.
Mueller et al., "The Influence of Glucan Polymer Structure and Solution Conformation on Binding to (1→3)-β-D-Glucan Receptors in a Human Monocyte-Like Cell Line," Glycobiology, 2000, 10(4):339-346.
Napolitano, "Immune stimulation in sepsis: to be or not to be?" Chest, 2005, 127:1882-1885.
Nasraway, "The problems and challenges of immunotherapy in sepsis," Chest, 2003, 123:451-459.
Onwe et al., "Lipid Profile and the Growing Concern on Lipid Related Diseases," IOSR Journal of Pharmacy and Biological Sciences (IOSR-JPBS), 2015, 10(5):22-27.
Park et al., "Antifibrotic Effects of a Polysaccharide Extracted from Ganoderma lucidum, Glycirrhizin, and Pentoxifylline in Rats with Cirrhosis Induced by Biliary Obstruction," Biol. Pharm. Bull, 1997, 20(4):417-420.
Peck-Palmer et al., "Deletion of MyD88 markedly attenuates sepsis-induced T and B lymphocyte apoptosis but worsens survival," Journal of Leukocyte Biology, 2008, 83:1009-1018.
Poedjomartono et al., "Khemoembolisasi transarterial pada kanker hati suatu kajian klinis dayaguna penambahan ekstrak ganoderma lucidum polysaccharide peptide beta-glucan secara oral," Universitas Gajah Mada, 2010, 2 pages (with English abstract).
Pourrojab et al., "Cross Talk of the First-Line Defense TLRs with PI3K/Akt Pathway, in Preconditioning Therapeutic Approach," Molecular and Cellular Therapies, 2015, 3:4.
Prasetya et al., "Ganodermalucidum polysaccharides peptide: possibility of hypertension therapy with antioxident," Journal of Hypertension, 2015, 33:e38.
Prasetya et al., "Polysaccharide peptide: a promising anti inflammation and anti oxidan in atherosclerosis," J Kardiol Indones., 2015, 36(1):22-27.
Qian et al., "Protective effects of betaglucin on myocardial tissue during myocardial infarction in rats and dogs," Acta Pharmacologica Sinica, 2009, 30:1092-1098.
Ramadori et al., "Physiology and Pathophysiology of Liver Inflammation, Damage and Repair," Journal of Physiology and Pharmacology, 2008, 107-117.
Rodeghiero et al., "Standardization of terminology, definitions and outcome criterian in immune thrombocytopeniaurpura of adults and children: report from an international working group," Blood, 2009, 113:2386-2393.
Ross, "Mechanisms of Disease: Atherosclerosis—An Inflammatory Disease," N Engl J Med., 1999, 340:115-126.
Rychlik et al., "The effectiveness of natural and synthetic immunomodulators in the treatment of inflammatory bowel disease in dogs," Acta Veterinaria Hungarica, Sep. 2013, 61(3):297-308.
Sadava et al., "Effect of Ganoderma on Drug-Sensitive and Multidrug-Resistant Small Cell Lung Carcinoma Cells," Cancer Letters, 2009, 277:182-189.

(56) References Cited

OTHER PUBLICATIONS

Santander et al., "Mechanisms of intrinsic resistance to antimicrobial peptides of Edwardsiella ictaluri and its influence on fish gut inflammation and virulence," Microbiology, 2013, 159(7):1471-86.

Sargowo et al., "Anti Inflammation and Anti Oxidant Effect of Active Agent Polysaccharide Peptide (*Ganoderma lucidum*) in Preventing Atherosclerotic Disease," Biomedical & Pharmacology Journal, 2015, 8(1):27-33.

Sargowo et al., "Potential development of polysaccharide peptide (ganoderma lucidum) as an anti-oxidant and anti-inflammation comprehensive therapy in cardiovascular diseases," Brawijaya University, 2016, 91 pages.

Sargowo et al., "Potential development of polysaccharide peptide (ganoderma lucidum) as antioxidant and anti-inflammatory in effort to comprehensive treatment of cardiovascular disease," Third Year Report, Brawijaya Univeristy, 2015, 121 pages.

Sargowo et al., "Potential development of polysaccharide peptide (ganoderma lucidum) as antioxidant and anti-inflammatory in effort to comprehensive treatment of cardiovascular disease," Second year report, Brawijaya Univeristy, 2015, 88 pages.

Sargowo et al., "PS 02-02: Effect Ganoderma lucidum polysaccharide peptides as anti-hypertension, anti-lipid, anti-oxidant, anti-inflammation in high risk patients of atherosclerosis," Journal of Hypertention, 2016, 34:e105.

Sargowo et al., "The effect of polysaccharide peptides (ganoderma lucidum) on the reduction of inflammation processes and oxidative stress in atherogenesis," Brawijaya Univeristy, 2013, 86 pages.

Sargowo, "PsP clinical study as complementary therapy in cardiovascular diseases," Brawijaya University, 2015, 1 page.

Sato et al., Tumor response evaluation criteria for HCC (hepatocellular carcinoma) treated using TACE (transcatheter arterial chemoembolization): RECIST (response evaluation criteria in solid tumors) version 1.1 and mRECIST (modified RECIST) : JIVROSG-0602, Upsala Journal of Medical Sciences, 2013, 118:16-22.

Satria et al., "The efficacy of polysaccharide peptides of Ganoderma lucidum to reduce endothelial dysfunction and dyslipidemia in high risk and stable andgia pectoris patients," Presented at Annual Scientific Meeting of Indonesian Heart Association, Jakarta, Indonesia, Apr. 15-17, 2016, 2 pages, abstract only.

Sawamura et al., "Abstracts of the 7th Asia Pacific Congress of Heart Failure and the Annual Scientific Meeting of Indonesian Heart Association," Presented in Bali, Indonesia, Apr. 17-19, 2014, European Journal of Heart Failure Supplements, 16(Suppl. 1):1-41.

Schiffrin EL. Oxidative Stress, Nitric Oxide Synthase and Superoxide Dismutase: A Matter of Imbalance Underlies Endothelial Dysfunction in the Human Coronary Circulation. Hypertension. 2008; 51:31-32.

Shi et al., "Antioxidant and immunoregulatory activity of Ganoderma lucidum polysaccharide (GLP)," Carbohydrate Polymers, Jun. 2013, 95(1):200-206, 5 pages.

Soetomo, "Immunomodulatory effect of polysaccharidepeptide (psp) from mycelium Ganoderma lucidum on lymphocyte apoptosis, mediated by TNF-a, IL10, HMGB1, HSP90, and ROS (experimental study of endotoxemai on male rate—sprague dawley)," University of Airlangga, 2016, 1 page (abstract only).

Sprague et al., "Inflammatory Cytokines in Vascular Dysfunction and Vascular Disease," Biochemical Pharmacol, 2009, 78(6):539-552.

Subhapriya et al., "Atherosclerosis: Critical Role of Oxidation and Inflammation," Int. J. Pharm Pharm Sci., 2013, 5(4):6-8.

Sudheesh et al., "Ganoderma lucidum ameliorate mitochondrial damage in isoproterenol-induces myocardial infarction in rats by enhancing the activities of TCA cycle enzymes and respiratory chain complexes," International Journal of Cardiology, 2013, 165(1):117-125.

Sugita, "Abstract 138: The Use of B-1.3-1.6-D-Glucan as Complementary Therapy for Cardiovascular Diseases," Circulation Research, 2014, 115:A138.

Sugita, "Abstract of clinical study of the use of B-1,3/1,6-Glucan (an Indonesian Ganoderma lucidum extract) in cardiovascular diseases," SLH Labs, (undated), Jul. 1, 2014, 2 pages.

Sugita, "Clinical study of the use of B-1,3/1,6-Glucan (an Indonesian Ganoderma lucidum extract) in cardiovascular diseases," Presentation presented at International Conference on Ganoderma Research, Fuzhou-China, Nov. 10-13, 2016, SLH Labs, 2 pages.

Tang et al., "A randomized, double blind and placebo controlled study of a Ganoderma lucidum polysaccharide extract in Neurasthenia," J Med Food., 2005, 8(1):53-58.

Thompson et al., "Does exercise increase HDL cholesterol in those who need it most?" Arterioscler Thromb Vasc Biol., 2001, 21:1097-1098.

U.S. Pharmacopeia beta-glucan reference standard, Catalog No. 1048288, Lot F0K129, 2019, 1 page.

Ubadillah et al., "The distinctive effect of polysaccharide peptides Ganoderma lucidum as anti atherogenesis in stable angia patients," Wolters Kluwer Health, 2016, e72: OS 10-03.

Ubadillah, "The prime effect of polysaccharide peptides to reduce endothelial dysfunction in high risk atherosclerotic patients," Poster, Presented at Clinical Forum, Monday, May 23, 2016, 1 page.

Vitryaturida et al., "The novel effect of B-D-Glucans extract of Ganoderma lucidum as antiinflammatory and antioxidative in stable angina patients," Poster Presentation at Annual Scientific Meeting of Indonesia Heart Association on Apr. 15-17, 2016, Jakarta, Indonesia, 7 pages.

Waty et al., "Effect of polysaccharide peptide (ganodermalucidum) against inflammatory processes focused on IL-6 and hsCRPin atherosclerosis," Journal of Hypertension, 2015, 1 page, abstract only.

Wei et al., "Activation of AP-1 and SP1 Correlates with Wound Growth Factor Gene Expression in Glucan-treated Human Fibroblast," International Immunopharmacology, 2002, 2:1163-1172.

Wei et al., "Glucan Stimulates Human Dermal Fibroblast Collagen Biosynthesis through a Nuclear Factor-1 Dependent Mechanism," Wound Repair and Regeneration, 2002, 10:161-168.

Weitberg "A Phase I/II Trial of Beta-(1,3)/(1,6)-D-Glucan in the Treatment of Patients with Advanced Malignancies Receiving Chemotherapy," Journal of Experimental and Clinical Cancer Research, 2008, 27(40):1-4.

Wihastuti et al., "Effects of subchronic exposure of PSP Ganoderma lucidum on a renal function and histopathology feature in Rattus novergicus Wistar strain," Natl. J. Physiol. Pharm. Pharmacol., 2015, 5(4):269-302.

Wihastuti et al., "Evaluation Subchronic Toxic Effect of Polysaccharide Peptide on Lipid and Hematologic Profile in Rattus norvegicus strain Wistar," Bangladesh Journal of Medical Science, 2016, 15(03), 8 pages.

Wihastuti et al., "Subchronic toxicity of Ganoderma lucidum polysaccharide peptide (PsP) to liver physiology and histopathologyImaging of liver on rattus norvegicus strain wistar rats," Biomedical & Pharmacology Journal, 2014, 7(2):417-424.

Wihastuti et al., "The reduction of aorta histopathological images through inhibition of reactive oxygen formation in hypercholesterolemia rattus norvegicus treated with polysaccharide peptide of Ganoderma lucidum," Iran J. Basic Med. Sci., 2015, 18(5):514-519.

Wilment et al., "Characterization of the Human β-Glucan Receptor and Its Alternatively Spliced Isoforms," The Journal of Biological Chemistry, 2001, 276(47):43818-43823.

Wink et al., "Nitric Oxide Protects Against Cellular Damage and Cytotoxicity From Reactive Oxygen Species," PNAS, 1993, 90:9813-9817.

Woo et al., "Ganoderma lucidum inhibits inducible nitric oxide synthase expression in macrophages," Molecular and Cellular Biochemistry, 2005, 275:165-171.

Xie et al., "Ganoderma lucidum Extract Inhibits Proliferation of SW 480 Human Colorectal Cancer Cells," Exp Oncol., 2006, 28(1):25-29.

Xu et al., "Ganoderma lucidum polysaccharides: immunomodulation and potential anti-tumor activities," American Journal of Chinese Medicine, 2011, 39(1):15-27.

(56) References Cited

OTHER PUBLICATIONS

Yang et al., "In Vitro and In Vivo Protective Effects of Proteoglycan Isolated From Mycelia of Ganoderma lucidum on Carbon Tetrachloride-induced Liver Injury," World J Gastroenterol., 2006, 12(9):1379-1385.

Yang et al., "The Emerging Role of Toll-Like Receptor 4 in Myocardial Inflammation," Cell Death and Disease, 2016, 7:e2234.

Ye et al., "A pilot study of Ganoderma lucidum in rheumatic arthritis," Proc Int Symposium Ganoderma Sci., 2001, 27-29.

You et al., "Protective effects of Ganoderma lucidum polysaccharides peptide on injury of macrophage induced by reactive oxygen species," Acta Pharmacol Sin., 2002, 23(9):787-791.

Zhang et al., "Extraction, characterization and antioxidant activity of polysaccharides of spent mushroom compost of Ganoderma lucidum," International Journal of Biological Macromolecules, Jan. 2016, 82:432-439, 4 pages.

Zhang et al., "Hypoglycemic effect of Ganoderma lucidum polysaccharides," Acta Pharmacologica Sinica, 2004, 25(2):191-195.

Zhang et al., "Role of TNF-alpha in vascular dysfunction," Clinical Science, 2009, 116:219-230.

Zhou et al., "A Phase I/II study of a Ganoderma lucidum extract in patients with coronary heart disease," International Journal of Medicinal Mushroom, 2004, 6:1-6.

Zhou et al., "The Immunomodulating Effect of Ganoderma lucidum (Curt: Fr.) P. Karst. (Ling Zhi, Reishi Mushroom) (*Aphyllophoromycetideae*)," International Journal of Medicinal Mushrooms, 2002, 4:1-11.

Zhu et al., "Promotion of Myelopoiesis in Myelosuppresses Mice by Ganoderma lucidum Polysaccharides," Front. Pharmacology, 2012, 3(20):1-7.

Zhu et al., "Ganoderma lucidum Polysaccharides Enhance the Function of Immunological Effector Cells in Immunosuppressed Mice," Journal of Ethnopharmacology, 2007, 111:219-226.

Angus et al., "Severe sepsis and septic shock," The New England Journal of Medicine, Aug. 2013, 36(9):840-851.

* cited by examiner

USE OF POLYSACCHARIDE FOR TREATING ST-ELEVATION MYOCARDIAL INFARCTION AND DISEASES OF THE DIGESTION SYSTEM

CROSS-REFERENCE TO RELATED APPLICATIONS

This application is a continuation of U.S. application Ser. No. 17/194,916, filed Mar. 8, 2021, now allowed, which is a continuation of U.S. application Ser. No. 15/806,048, filed Nov. 7, 2017, now U.S. Pat. No. 10,940,162, which claims the benefit of U.S. Provisional Application Ser. No. 62/419, 174, filed Nov. 8, 2016, and 62/553,647, filed Sep. 1, 2017, the disclosures of which are incorporated herein by reference in their entireties.

TECHNICAL FIELD

This invention relates to the therapeutic treatment of ST-elevation myocardial infarction (STEMI) and diseases of the digestion system using β-1,3/1,6-D-glucan derived from mycelium extract of *Ganoderma lucidum*.

BACKGROUND

Heart disease is one of the leading causes of mortality globally. Every year in the US 610,000 people die of heart disease, which is approximately 1 in 4 deaths. Coronary heart disease (CHD) is the most common type of heart disease, killing over 370,000 people annually (see e.g., Underlying Cause of Death 1999-2013 on CDC WONDER Online Database, released 2015). Factors such as smoking, fat and cholesterol level in the blood, hypertension, obesity, and high blood glucose level due to diabetes play an important role in the occurrence of coronary heart disease. When heart damage occurs, the body begins the healing process of the wounds by forming plaque in the injured arteries. Additional factors may also increase the risk of atherosclerosis, for example high levels of blood cholesterol, high blood pressure, smoking, insulin resistance, diabetes, obesity, and lack of physical activity.

SUMMARY

The present application provides, inter alia, methods of treating a disease of the digestive system in a subject in need thereof, comprising administering to the subject a therapeutically effective amount of β-1,3/1,6-D-glucan, or a pharmaceutically acceptable salt thereof.

In some embodiments, the disease of the digestive system comprises inflammation of one or more organs of the digestive system. In some embodiments, the disease of the digestive system is selected from the group consisting of inflammatory bowel disease, Crohn's disease, and ulcerative colitis.

The present application further provides methods of treating ST-elevation myocardial infarction in a subject in need thereof, comprising administering to the subject a therapeutically effective amount of β-1,3/1,6-D-glucan, or a pharmaceutically acceptable salt thereof.

In some embodiments, the methods comprise administering about 500 mg to about 600 mg β-1,3/1,6-D-glucan, or a pharmaceutically acceptable salt thereof, to the subject. In some embodiments, the methods comprise administering about 500 mg to about 550 mg β-1,3/1,6-D-glucan, or a pharmaceutically acceptable salt thereof, to the subject.

The present application further provides methods of treating a disease of the digestive system in a subject in need thereof, comprising administering to the subject a pharmaceutical composition comprising β-1,3/1,6-D-glucan, or a pharmaceutically acceptable salt thereof, and one or more pharmaceutically acceptable excipients.

The present application further provides methods of treating ST-elevation myocardial infarction in a subject in need thereof, comprising administering to the subject a pharmaceutical composition comprising β-1,3/1,6-D-glucan, or a pharmaceutically acceptable salt thereof, and one or more pharmaceutically acceptable excipients.

In some embodiments, the pharmaceutical composition comprises about 500 mg to about 600 mg of the β-1,3/1,6-D-glucan, or a pharmaceutically acceptable salt thereof. In some embodiments, the pharmaceutical composition comprises about 500 mg to about 550 mg of the β-1,3/1,6-D-glucan, or a pharmaceutically acceptable salt thereof.

The present application further provides methods of treating inflammatory bowel disease in a subject in need thereof, comprising administering to the subject about 500 mg to about 600 mg of β-1,3/1,6-D-glucan, or a pharmaceutically acceptable salt thereof.

The present application further provides methods of treating Crohn's disease in a subject in need thereof, comprising administering to the subject about 500 mg to about 600 mg of β-1,3/1,6-D-glucan, or a pharmaceutically acceptable salt thereof.

The present application further provides methods of treating ulcerative colitis in a subject in need thereof, comprising administering to the subject about 500 mg to about 600 mg of β-1,3/1,6-D-glucan, or a pharmaceutically acceptable salt thereof.

The present application further provides methods of treating ST-elevation myocardial infarction in a subject in need thereof, comprising administering to the subject about 500 mg to about 600 mg of β-1,3/1,6-D-glucan, or a pharmaceutically acceptable salt thereof.

The present application further provides methods of treating inflammatory bowel disease in a subject in need thereof, comprising administering to the subject a pharmaceutical composition comprising about 500 mg to about 600 mg of β-1,3/1,6-D-glucan, or a pharmaceutically acceptable salt thereof, and one or more pharmaceutically acceptable excipients.

The present application further provides methods of treating Crohn's disease in a subject in need thereof, comprising administering to the subject a pharmaceutical composition comprising about 500 mg to about 600 mg of β-1,3/1,6-D-glucan, or a pharmaceutically acceptable salt thereof, and one or more pharmaceutically acceptable excipients.

The present application further provides methods of treating ulcerative colitis in a subject in need thereof, comprising administering to the subject a pharmaceutical composition comprising about 500 mg to about 600 mg of β-1,3/1,6-D-glucan, or a pharmaceutically acceptable salt thereof, and one or more pharmaceutically acceptable excipients.

The present application further provides methods of treating ST-elevation myocardial infarction in a subject in need thereof, comprising administering to the subject a pharmaceutical composition comprising about 500 mg to about 600 mg of 3-1,3/1,6-D-glucan, or a pharmaceutically acceptable salt thereof, and one or more pharmaceutically acceptable excipients.

The present application further provides methods of treating one or more symptoms of a disease of the digestive system in a subject in need thereof, comprising: a) identifying or having identified a subject as exhibiting one or more symptoms of the disease of the digestive system; and b) administering to the subject a therapeutically effective amount of β-1,3/1,6-D-glucan, or a pharmaceutically acceptable salt thereof.

In some embodiments, the subject is identified or has been identified as exhibiting inflammation associated with a disease of the digestive system. In some embodiments, the subject is identified or has been identified as exhibiting one or more symptoms associated with a disease of the digestive system selected from the group consisting of inflammatory bowel disease, Crohn's disease, and ulcerative colitis.

The present application further provides methods of treating one or more symptoms of ST-elevation myocardial infarction in a subject in need thereof, comprising: a) identifying or having identified a subject as exhibiting one or more symptoms of the ST-elevation myocardial infarction; and b) administering to the subject a therapeutically effective amount of β-1,3/1,6-D-glucan, or a pharmaceutically acceptable salt thereof.

In some embodiments, the methods comprise administering about 500 mg to about 600 mg β-1,3/1,6-D-glucan, or a pharmaceutically acceptable salt thereof, to the subject. In some embodiments, the method comprises administering about 500 mg to about 550 mg β-1,3/1,6-D-glucan, or a pharmaceutically acceptable salt thereof, to the subject.

The present application further provides methods of treating one or more symptoms of a disease of the digestive system in a subject in need thereof, comprising: a) identifying or having identified a subject as exhibiting one or more symptoms of the disease of the digestive system; and b) administering to the subject a pharmaceutical composition comprising β-1,3/1,6-D-glucan, or a pharmaceutically acceptable salt thereof, and one or more pharmaceutically acceptable excipients.

In some embodiments, the subject is identified or has been identified as exhibiting inflammation associated with a disease of the digestive system. In some embodiments, the subject is identified or has been identified as exhibiting one or more symptoms associated with a disease of the digestive system selected from the group consisting of inflammatory bowel disease, Crohn's disease, and ulcerative colitis.

The present application further provides methods of treating one or more symptoms of ST-elevation myocardial infarction in a subject in need thereof, comprising: a) identifying or having identified a subject as exhibiting one or more symptoms of the ST-elevation myocardial infarction; and b) administering to the subject a pharmaceutical composition comprising β-1,3/1,6-D-glucan, or a pharmaceutically acceptable salt thereof, and one or more pharmaceutically acceptable excipients.

In some embodiments, the pharmaceutical composition comprises about 500 mg to about 600 mg of the β-1,3/1,6-D-glucan, or a pharmaceutically acceptable salt thereof. In some embodiments, the pharmaceutical composition comprises about 500 mg to about 550 mg of the β-1,3/1,6-D-glucan, or a pharmaceutically acceptable salt thereof.

In some embodiments, the methods further comprise identifying or having identified the subject as exhibiting abnormal expression of one or more cytokines. In some embodiments, the subject is identified or has been identified as exhibiting abnormal expression of interleukin-6, interleukin-10, tumor necrosis factor-α, C-reactive protein, or any combination thereof.

In some embodiments, the methods further comprise administering one or more additional therapeutic agents.

In some embodiments, about 5 mg/kg/day to about 10 mg/kg/day of the β-1,3/1,6-D-glucan is administered to the subject. In some embodiments, about 7 mg/kg/day to about 10 mg/kg/day of the β-1,3/1,6-D-glucan is administered to the subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Figure 1:
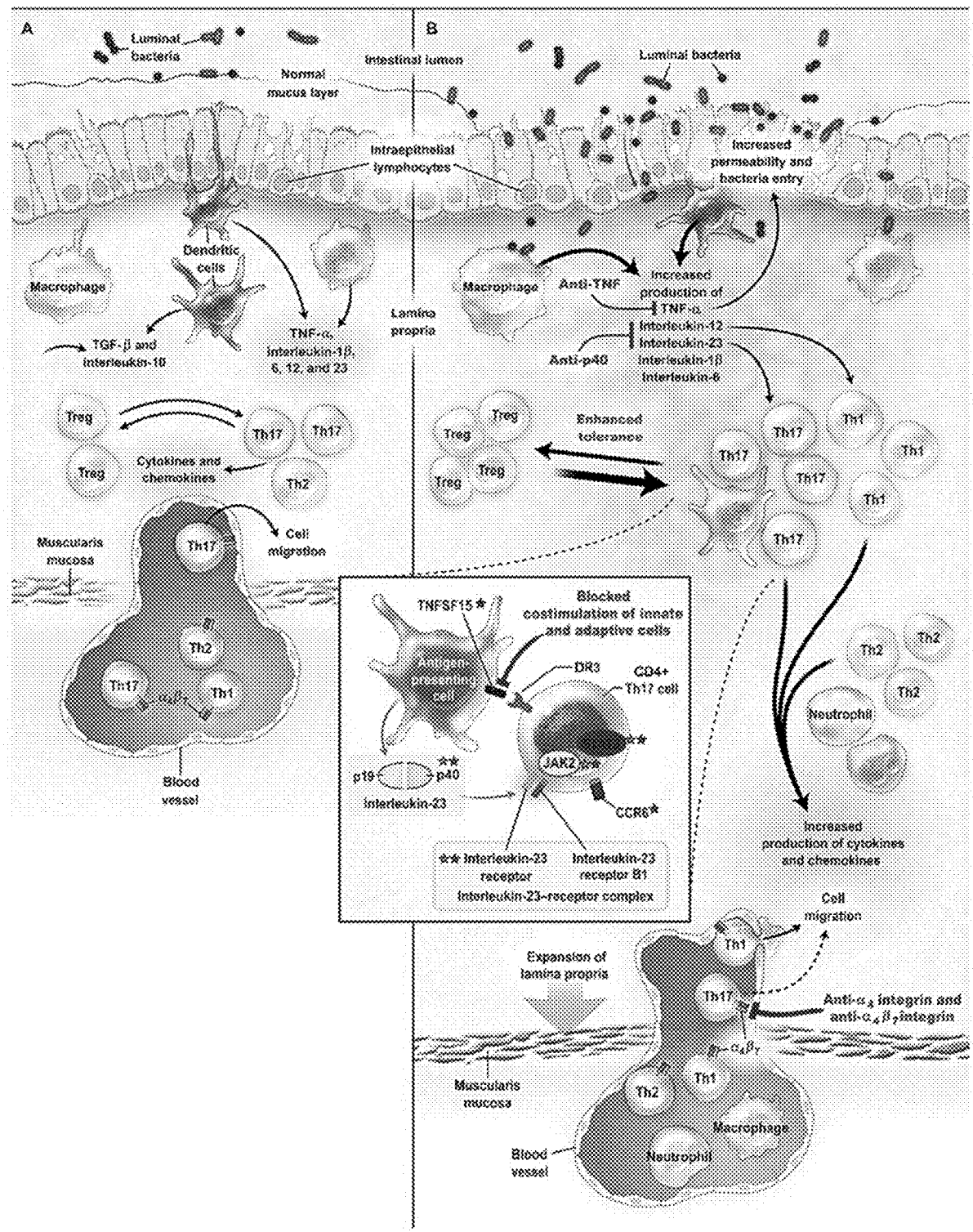
FIG. 1 shows representative illustration of the *Lamina propria* in a healthy subject (Panel A) and several cellular events which contribute to increased bacterial adherence to epithelial cells (Panel B).

*Ganoderma lucidum* is a genus of polypore fungus that grows on wood and consists of about 80 species, which are generally found in tropical environments (Krik et al, *Dictionary of the Fungi*, 10th Ed, CABI Europe, 2008). Several classes of bioactive substances isolated and identified from *G. lucidum* such as triterpenoids, polysaccharides, nucleosides, sterols, and alkaloids have been shown to function as anti-inflammatory agents, anti-tumor agents, antioxidant agents, immunomodulators, and radioprotection agents (see e.g., Xu et al, *American Journal of Chinese Medicine*, 2011, 39(1):15-27). The present application provides polysaccharides, derived from *Ganoderma lucidum* mycelium which comprise β-1,3/1,6-D-glucan as an active component (e.g., an active component towards treating the diseases provided herein). β-D-glucans are major components of *Ganoderma* mycelium, which, in the spores of *Ganoderma*, is a minor component (Chan et al, *Journal of Hematology & Oncology*, 2009, 2:25).

Previous studies regarding the function and role of bioactive polysaccharides have demonstrated that β-1,3/1,6-D-glucan exhibits properties including anti-inflammatory, anti-tumor, antioxidant, and immunomodulating radioprotection (see e.g., Xu et al, *American Journal of Chinese Medicine*, 2011, 39(1):15-27). For example, orally administered β-glucans have been shown to be taken up (i.e., phagocytized) by macrophages in Peyer Patch's via the Dectin-1 receptor and were subsequently transported to the spleen, lymph nodes, and bone marrow. Within the bone marrow, the macrophages defragmented the large β-1,3-glucan molecule into smaller soluble β-1,3-glucan fragments. The small β-glucan fragments were then released by the macrophages and taken up by the circulating granulocytes, monocytes and dendritic cells. Despite low systemic blood levels (less than 0.5%), significant systemic immunomodulating effects in terms of humoral and cellular immune responses were demonstrated (see e.g., Chan et al, *Journal of Hematology & Oncology*, 2009, 2(25):1-11). In addition, β-1,3/1,6-D-glucan effects a variety of membrane receptors found in the immune cells such as: Dectin-1, Complement Receptor-3 (CR-3), Toll-Like Receptor (TLR), Scavenger Receptor, Lactosylceramide Receptor and Langerin Receptor (see e.g., Chan et al, *Journal of Hematology & Oncology*, 2009, 2(25):1-11; and Clark et al, *Biology and Chemistry of β-Glucan*, 2011, 1:19-38) A number of reports have demonstrated that *Ganoderma lucidum* Polysaccharide Peptide (GLPP) modulates immune function both in vivo and in vitro. The immunomodulating effects of GLPP are extensive, including promoting the function of Antigen Presenting-Cell (APC), mononuclear phagocyte system, humoral and cellular immunity (see e.g., Lin et al., *J. Pharmacol. Sci.* 2005, 99:144-153), which is useful for treatment of the diseases provided herein.

In addition, the β-1,3/1,6-D-glucan described herein can increase the activity of superoxide dismutase (SOD) and catalase (CAT) (Jia et al, *Food Chemistry*, 2008, 115:32-36), which is useful for treatment of the disease provided herein. Cellular oxidative damage has been known as a major cause of cells and tissues injury and is primarily caused by Reactive Oxygen Species (ROS) that binds to many normal cell components, reacts with unsaturated lipid membranes, denatures the protein and attacks nucleic acid. As a result of the active metabolic oxygen formation imbalance and an elimination of both enzymatic and non-enzymatic antioxidants, this process is called an oxidative stress. Oxidative stress plays an important role in physiological conditions and also various diseases such as diabetes mellitus, myocardial infarction and carcinogenesis. The cells in the body possess antioxidant mechanism such as glucose-6-phosphate dehydrogenase, superoxide dismutase (SOD), catalase (CAT), glutathione-S-transferase (GST), which are useful to prevent the formation of free radicals and repair of oxidative damage. SOD and CAT are major enzymes that eliminate the poison of free radical scavenger of in vivo. SOD enzyme adopts superoxide radicals ($O_2$) and catalyzes the conversion of these two radicals to form molecular hydrogen and oxygen peroxidase. Hydrogen peroxidase is formed by SOD and other processes by CAT. Additional uses of the β-1,3/1,6-D-glucan described herein are described, for example, in Appendix A of U.S. Provisional Patent Application No. 62/553,647, the disclosure of which is incorporated herein by reference in its entirety.

In some embodiments, the polysaccharide comprises about 30% to about 80% total glucan, for example, about 30% to about 80%, about 30% to about 70%, about 30% to about 60%, about 30% to about 50%, about 30% to about 40%, about 40% to about 80%, about 40% to about 70%, about 40% to about 60%, about 40% to about 50%, about 50% to about 80%, about 50% to about 70%, about 50% to about 60%, about 60% to about 80%, about 60% to about 70%, or about 70% to about 80% total glucan.

In some embodiments, the molecular weight of the polysaccharide is from about 3600 kDa to about 4200 kDa, for example, about 3600 kDa to about 4200 kDa, about 3800 kDa to about 4200 kDa, about 4000 kDa to about 4200 kDa, about 3800 kDa to about 4200 kDa, about 4000 kDa to about 4200 kDa, or about 4000 kDa to about 4200 kDa.

In some embodiments, the total glucan comprises β-glucan and α-glucan. In some embodiments, the total glucan consists essentially of β-glucan. In some embodiments, the total glucan comprises greater than about 90% β-glucan, greater than about 95% β-glucan, greater than about 96% β-glucan, greater than about 97% β-glucan, greater than about 98% β-glucan, greater than about 99% β-glucan, greater than about 99.1% β-glucan, greater than about 99.2% β-glucan, greater than about 99.3% β-glucan, greater than about 99.4% β-glucan, greater than about 99.5% β-glucan, greater than about 99.6% β-glucan, greater than about 99.7% β-glucan, greater than about 99.8% β-glucan, or greater than about 99.9% β-glucan.

In some embodiments, the ratio of 1,3- to 1,6-glucan linkages in the β-1,3/1,6-D-glucan is from about 1:1 to about 3:1. In some embodiments, the ratio of 1,3- to 1,6-glucan linkages in the β-1,3/1,6-D-glucan is about 2:1.

In some embodiments, the glycosyl composition of the polysaccharide comprising the β-1,3/1,6-D-glucan comprises saccharides is selected from the group consisting of fucose, xylose, mannose, galactose, and glucose. In some embodiments, the glycosyl composition of the polysaccharide is as shown in Table 1B. In some embodiments, the glycosyl linkages of the polysaccharide is as shown in Table 2. In some embodiments, the polysaccharide consists essentially of β-1,3/1,6-D-glucan. In some embodiments, the glycosyl composition of the polysaccharide is as shown in Table 1B and the glycosyl linkages of the polysaccharide are as shown in Table 2.

In some embodiments, the polysaccharide comprises one or more terminal fucopyranosyl groups, one or more terminal xylopyranosyl groups, one or more terminal mannopyranosyl groups, one or more terminal glucopyranosyl groups, one or more 2-xylopyranosyl groups, one or more 3-glucopyranosyl groups, one or more 2-mannopyranosyl groups, one or more 3-linked mannopyranosyl groups, one or more 2-glucopyranosyl groups, one or more 4-mannopyranosyl groups, one or more 6-glucopyranosyl groups, one or more 4-glucopyranosyl groups, one or more 2,3-mannopyranosyl groups, one or more 3,4-mannopyranosyl groups, one or more 3,4-glucopyranosyl groups, one or more 2,3-glucopyranosyl groups, one or more 2,4-glucopyranosyl groups, one or more 3,6-glucopyranosyl groups, one or more 4,6-galactopyranosyl groups, one or more 2,3,4-glucopyranosyl groups, one or more 3,4,6-glucopyranosyl groups, and one or more 2,3,6-glucopyranosyl groups.

In some embodiments, the polysaccharide consists essentially of one or more terminal fucopyranosyl groups, one or more terminal xylopyranosyl groups, one or more terminal mannopyranosyl groups, one or more terminal glucopyranosyl groups, one or more 2-xylopyranosyl groups, one or more 3-glucopyranosyl groups, one or more 2-mannopyranosyl groups, one or more 3-linked mannopyranosyl groups, one or more 2-glucopyranosyl groups, one or more 4-mannopyranosyl groups, one or more 6-glucopyranosyl groups, one or more 4-glucopyranosyl groups, one or more 2,3-mannopyranosyl groups, one or more 3,4-mannopyranosyl groups, one or more 3,4-glucopyranosyl groups, one or more 2,3-glucopyranosyl groups, one or more 2,4-glucopyranosyl groups, one or more 3,6-glucopyranosyl groups, one or more 4,6-galactopyranosyl groups, one or more 2,3,4-glucopyranosyl groups, one or more 3,4,6-glucopyranosyl groups, and one or more 2,3,6-glucopyranosyl groups.

In some embodiments, the polysaccharide consists of one or more terminal fucopyranosyl groups, one or more terminal xylopyranosyl groups, one or more terminal mannopyranosyl groups, one or more terminal glucopyranosyl groups, one or more 2-xylopyranosyl groups, one or more 3-glucopyranosyl groups, one or more 2-mannopyranosyl groups, one or more 3-linked mannopyranosyl groups, one or more 2-glucopyranosyl groups, one or more 4-mannopyranosyl groups, one or more 6-glucopyranosyl groups, one or more 4-glucopyranosyl groups, one or more 2,3-mannopyranosyl groups, one or more 3,4-mannopyranosyl groups, one or more 3,4-glucopyranosyl groups, one or more 2,3-glucopyranosyl groups, one or more 2,4-glucopyranosyl groups, one or more 3,6-glucopyranosyl groups, one or more 4,6-galactopyranosyl groups, one or more 2,3,4-glucopyranosyl groups, one or more 3,4,6-glucopyranosyl groups, and one or more 2,3,6-glucopyranosyl groups.

In some embodiments, the polysaccharide comprising the β-1,3/1,6-D-glucan provided herein, or pharmaceutically acceptable salt thereof, is substantially isolated. The term "substantially isolated" means that the polysaccharide is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. General methods for isolating compounds and their salts are routine in the art. In some embodiments, the polysaccharide is isolated according to the methods described in Indonesian Patent Application No. P-00 2011 00579, the disclosure of which is incorporated herein by reference in its entirety. In some embodiments, the polysaccharide comprising the β-1,3/1,6-D-glucan further comprises α-1,3/1,6-D-glucan.

The present invention further provides use of the β-1,3/1,6-D-glucan described herein, or a pharmaceutically acceptable salt thereof, for the preparation of a medicament for use in any of the methods described herein.

ST-Elevation Myocardial Infarction (STEMI)

The present application provides, inter alia, methods of treating ST-elevation myocardial infarction (STEMI) in a subject in need thereof, comprising administering to the subject a therapeutically effective amount of β-1,3/1,6-D-glucan, or a pharmaceutically acceptable salt thereof. In some embodiments, β-1,3/1,6-D-glucan is administered to the subject. In some embodiments, the polysaccharide comprising the β-1,3/1,6-D-glucan is administered to the subject.

STEMI usually occurs when the coronary blood flow decreases abruptly after thrombus occlusion on the preexisted arteriosclerotic plaque. For example, STEMI occurs when coronary artery thrombosis occurs rapidly at the site of vascular injury, where the injury may be exacerbated by factors such as smoking, hypertension, and lipid accumulation. In many cases, infarction occurs when atherosclerotic plaque experiences fissures, rupture, or ulceration. If local or systemic conditions trigger thrombogenesis, mural thrombus will develop on the location of the rupture, resulting in coronary artery occlusion. Histological studies have shown that coronary plaque is prone to rupture if it has a thin fibrous cap and a lipid-rich core. In STEMI, classic pathological features include a fibrin rich red thrombus, which without being bound by theory, is believed to be one of the reasons why STEMI responds to thrombolytic therapy. At the location of plaque rupture, various agonists (e.g., collagen, ADP, epinephrine, serotonin) trigger the activation of platelets, which in turn produce and release thromboxane A2 (a local potent vasoconstrictor). The activation of thrombosis also generates a conformational change in the receptor glycoprotein IIb/IIIa. After experiencing a conversion on its function, the receptor has a high affinity for the amino acid sequence in a soluble adhesion protein (integrins) such as von Willebrand factor (vWF) and fibrinogen, both of which are multivalent molecules that can bind two different platelets simultaneously, resulting in a cross linking of platelets and aggregation. The cascade coagulation is activated by the exposure of tissue factor in the damaged endothelial cells. Activated Factors VII and X will result in the conversion of prothrombin into thrombin, which then will convert fibrinogen to fibrin. The involved coronary arteries will then experience an occlusion by thrombus composed of platelet and fibrin aggregates. In some circumstances, STEMI may also result from coronary embolism, congenital abnormalities, coronary spasm, and various systemic inflammatory diseases (see e.g., Alwi et al, *Internal Medicine*, vol. II, ed. VI, Ch. 191; pp: 1459-1460; InternaPublishing, Jakarta (2014)).

The present application further provides methods of treating one or more symptoms of ST-elevation myocardial infarction in a subject in need thereof, comprising: a) identifying or having identified a subject as exhibiting one or more symptoms of the ST-elevation myocardial infarction;

and b) administering to the subject a therapeutically effective amount of β-1,3/1,6-D-glucan, or a pharmaceutically acceptable salt thereof.

In some embodiments, the method comprises administering about 10 mg to about 1 g β-1,3/1,6-D-glucan, or a pharmaceutically acceptable salt thereof, to the subject, for example, about 10 mg to about 1 g, about 10 mg to about 800 mg, about 10 mg to about 600 mg, about 10 mg to about 400 mg, about 10 mg to about 200 mg, about 10 mg to about 100 mg, about 10 mg to about 50 mg, about 50 mg to about 1 g, about 50 mg to about 800 mg, about 50 mg to about 600 mg, about 50 mg to about 400 mg, about 50 mg to about 200 mg, about 50 mg to about 100 mg, about 100 mg to about 1 g, about 100 mg to about 800 mg, about 100 mg to about 600 mg, about 100 mg to about 400 mg, about 100 mg to about 200 mg, about 200 mg to about 1 g, about 200 mg to about 800 mg, about 200 mg to about 600 mg, about 200 mg to about 400 mg, about 400 mg to about 1 g, about 400 mg to about 800 mg, about 400 mg to about 600 mg, about 600 mg to about 1 g, about 600 mg to about 800 mg, or about 800 mg to about 1 g. In some embodiments, the method comprises administering about 500 mg to about 600 mg β-1,3/1,6-D-glucan, or a pharmaceutically acceptable salt thereof, to the subject. In some embodiments, the method comprises administering about 500 mg to about 550 mg β-1,3/1,6-D-glucan, or a pharmaceutically acceptable salt thereof, to the subject.

The present application further provides methods of treating ST-elevation myocardial infarction in a subject in need thereof, comprising administering to the subject about 500 mg to about 600 mg of β-1,3/1,6-D-glucan, or a pharmaceutically acceptable salt thereof. In some embodiments, about 500 mg to about 600 mg of β-1,3/1,6-D-glucan is administered to the subject.

In some embodiments, about 1 mg/kg/day to about 20 mg/kg/day of the β-1,3/1,6-D-glucan, or a pharmaceutically acceptable salt thereof, is administered to the subject, for example, about 1 mg/kg/day to about 20 mg/kg/day, about 1 mg/kg/day to about 15 mg/kg/day, about 1 mg/kg/day to about 10 mg/kg/day, about 1 mg/kg/day to about 5 mg/kg/day, about 5 mg/kg/day to about 20 mg/kg/day, about 5 mg/kg/day to about 15 mg/kg/day, about 5 mg/kg/day to about 10 mg/kg/day, about 10 mg/kg/day to about 20 mg/kg/day, about 10 mg/kg/day to about 15 mg/kg/day, or about 15 mg/kg/day to about 20 mg/kg/day. In some embodiments, about 5 mg/kg/day to about 10 mg/kg/day of the β-1,3/1,6-D-glucan, or a pharmaceutically acceptable salt thereof, is administered to the subject. In some embodiments, about 5 mg/kg/day to about 10 mg/kg/day of the 0-1,3/1,6-D-glucan is administered to the subject. In some embodiments, about 7 mg/kg/day to about 10 mg/kg/day of the β-1,3/1,6-D-glucan, or a pharmaceutically acceptable salt thereof, is administered to the subject. In some embodiments, about 7 mg/kg/day to about 10 mg/kg/day of the β-1,3/1,6-D-glucan is administered to the subject.

In some embodiments, the methods provided herein further comprise modulating one or more cytokines or an activity associated with one or more cytokines in the subject, comprising contacting a cell or tissue associated with abnormal expression of the one or more cytokines with β-1,3/1,6-D-glucan, or a pharmaceutically acceptable salt thereof. In some embodiments, the modulating is inhibition. In some embodiments, the modulating is activation. In some embodiments, the contacting is performed in vitro. In some embodiments, the contacting is performed in vivo. In some embodiments, the methods comprise modulating one or more cytokines selected from the group consisting of interleukin-6, interleukin-10, tumor necrosis factor-α, C-reactive protein, or any combination thereof, in the subject. In some embodiments, the methods comprise modulating one or more cytokine activities in the subject. In some embodiments, the methods provided herein further comprise identifying the subject, or having the subject identified, as exhibiting abnormal expression of one or more cytokines. In some embodiments, the subject is identified or has been identified as exhibiting abnormal expression of interleukin-6, interleukin-10, tumor necrosis factor-α, C-reactive protein, or any combination thereof. In some embodiments, the cell or tissue is contacted with β-1,3/1,6-D-glucan.

In some embodiments, the methods provided herein further comprise modulating myosin in the subject, comprising contacting a cell or tissue associated with abnormal expression of myosin with β-1,3/1,6-D-glucan, or a pharmaceutically acceptable salt thereof.

In some embodiments, the methods provided herein further comprise modulating one or more of MDA, SOD, IL-6, hsCRP, TNF-α, total cholesterol, triglycerides (TG), low-density lipids (LDL), high-density lipids (HDL), fasting glucose, HbA1c, systolic BP, diastolic BP, the ratio of EPC-CEC, or any combination thereof, in the subject.

Diseases of the Digestive System Idiopathic inflammatory bowel disease comprises two types of chronic intestinal disorders, Crohn's disease (CD), and ulcerative colitis (UC). Accumulating evidence suggests that inflammatory bowel disease results from inappropriate inflammatory response to intestinal microbes in a genetically susceptible host. As shown in FIG. 1, the *lamina propria* normally contains a diverse array of immune cells and secreted cytokines. These include anti-inflammatory mediators (transforming growth factor β [TGF-β] and interleukin-10 [IL-10]) that downregulate immune responses, as well as pro-inflammatory mediators from both innate and adaptive immune cells that limit excessive entry of intestinal microbiota and defend against pathogens. Non-inflammatory defenses, such as phagocytosis by macrophages, are believed to assist in defending against bacteria entering the *lamina propria* while minimizing tissue injury. A homeostatic balance is maintained between regulatory T cells (e.g., Treg) and effector cells (Th1, Th2, and Th17).

Several events contribute to increased bacterial adherence to epithelial cells. In inflammatory bowel disease (IBD), innate cells produce increased levels of Tumor Necrosis Factor α (TNF-α), interleukin-11, interleukin-6, interleukin-12, interleukin-23, and chemokines. There is marked expansion of the *lamina propria*, with increased numbers of CD4+ T cells, especially proinflammatory T-cell subgroups, which also secrete increased levels of cytokines and chemokines. Increased production of chemokines results in recruitment of additional leukocytes, resulting in a cycle of inflammation.

Accordingly, the present application provides methods of treating a disease of the digestive system in a subject in need thereof, comprising administering to the subject a therapeutically effective amount of β-1,3/1,6-D-glucan, or a pharmaceutically acceptable salt thereof. Example diseases of the digestive system include, but are not limited to, inflammatory bowel disease, Crohn's disease, and ulcerative colitis. In some embodiments, β-1,3/1,6-D-glucan is administered to the subject. In some embodiments, a polysaccharide comprising β-1,3/1,6-D-glucan is administered to the subject.

In some embodiments, the disease is associated with an abnormal inflammatory response of the digestive system. In some embodiments, the disease is associated with an abnormal inflammatory response of one or more organs of the digestive system (e.g., esophagus, stomach, small intestine, and large intestine). In some embodiments, the disease is associated with an abnormal inflammatory response of one or more organs associated with the digestive system (e.g., tongue, salivary glands, pancreas, liver, gallbladder, and the like). In some embodiments, the disease of the digestive system comprises inflammation of one or more organs of the digestive system. In some embodiments, the disease of the digestive system comprises inflammation of one or more organs associated with the digestive system. In some embodiments, the disease of the digestive system comprises inflammation of one or more organs selected from the group consisting of the esophagus, stomach, small intestine, large intestine, tongue, salivary glands, pancreas, liver, and gallbladder. In some embodiments, the disease is selected from the group consisting of inflammatory bowel disease, Crohn's disease, and ulcerative colitis, or inflammation associated with any of the aforementioned diseases.

The present application further provides methods of treating a disease selected from the group consisting of sepsis, idiopathic thrombocytopenic purpura (ITP), myasthenia gravis, pseudobulbar palsy, military tuberculosis, myocarditis, and cancer.

In some embodiments, the cancer is selected from the group consisting of non-small cell lung carcinoma (NSCLC) and brain cancer. In some embodiments, the cancer is a solid tumor.

In some embodiments, the methods comprise administering about 10 mg to about 1 g β-1,3/1,6-D-glucan, or a pharmaceutically acceptable salt thereof, to the subject, for example, about 10 mg to about 1 g, about 10 mg to about 800 mg, about 10 mg to about 600 mg, about 10 mg to about 400 mg, about 10 mg to about 200 mg, about 10 mg to about 100 mg, about 10 mg to about 50 mg, about 50 mg to about 1 g, about 50 mg to about 800 mg, about 50 mg to about 600 mg, about 50 mg to about 400 mg, about 50 mg to about 200 mg, about 50 mg to about 100 mg, about 100 mg to about 1 g, about 100 mg to about 800 mg, about 100 mg to about 600 mg, about 100 mg to about 400 mg, about 100 mg to about 200 mg, about 200 mg to about 1 g, about 200 mg to about 800 mg, about 200 mg to about 600 mg, about 200 mg to about 400 mg, about 400 mg to about 1 g, about 400 mg to about 800 mg, about 400 mg to about 600 mg, about 600 mg to about 1 g, about 600 mg to about 800 mg, or about 800 mg to about 1 g. In some embodiments, the method comprises administering about 500 mg to about 600 mg β-1,3/1,6-D-glucan, or a pharmaceutically acceptable salt thereof, to the subject. In some embodiments, the method comprises administering about 500 mg to about 550 mg β-1,3/1,6-D-glucan, or a pharmaceutically acceptable salt thereof, to the subject.

The present application further provides methods of treating inflammatory bowel disease in a subject in need thereof, comprising administering to the subject about 500 mg to about 600 mg of β-1,3/1,6-D-glucan, or a pharmaceutically acceptable salt thereof. In some embodiments, about 500 mg to about 600 mg of β-1,3/1,6-D-glucan is administered to the subject.

The present application further provides methods of treating Crohn's disease in a subject in need thereof, comprising administering to the subject about 500 mg to about 600 mg of β-1,3/1,6-D-glucan, or a pharmaceutically acceptable salt thereof. In some embodiments, about 500 mg to about 600 mg of β-1,3/1,6-D-glucan is administered to the subject.

The present application further provides methods of treating ulcerative colitis in a subject in need thereof, comprising administering to the subject about 500 mg to about 600 mg of β-1,3/1,6-D-glucan, or a pharmaceutically acceptable salt thereof. In some embodiments, about 500 mg to about 600 mg of β-1,3/1,6-D-glucan is administered to the subject.

In some embodiments, about 1 mg/kg/day to about 20 mg/kg/day of the β-1,3/1,6-D-glucan, or a pharmaceutically acceptable salt thereof, is administered to the subject, for example, about 1 mg/kg/day to about 20 mg/kg/day, about 1 mg/kg/day to about 15 mg/kg/day, about 1 mg/kg/day to about 10 mg/kg/day, about 1 mg/kg/day to about 5 mg/kg/day, about 5 mg/kg/day to about 20 mg/kg/day, about 5 mg/kg/day to about 15 mg/kg/day, about 5 mg/kg/day to about 10 mg/kg/day, about 10 mg/kg/day to about 20 mg/kg/day, about 10 mg/kg/day to about 15 mg/kg/day, or about 15 mg/kg/day to about 20 mg/kg/day. In some embodiments, about 5 mg/kg/day to about 10 mg/kg/day of the β-1,3/1,6-D-glucan, or a pharmaceutically acceptable salt thereof, is administered to the subject. In some embodiments, about 5 mg/kg/day to about 10 mg/kg/day of the 0-1,3/1,6-D-glucan is administered to the subject. In some embodiments, about 7 mg/kg/day to about 10 mg/kg/day of the β-1,3/1,6-D-glucan, or a pharmaceutically acceptable salt thereof, is administered to the subject. In some embodiments, about 7 mg/kg/day to about 10 mg/kg/day of the β-1,3/1,6-D-glucan is administered to the subject.

In some embodiments, the methods provided herein further comprise modulating one or more cytokines or an activity associated with one or more cytokines in the subject, comprising contacting a cell or tissue associated with abnormal expression of the one or more cytokines with β-1,3/1,6-D-glucan, or a pharmaceutically acceptable salt thereof. In some embodiments, the modulating is inhibiting. In some embodiments, the modulating is activating. In some embodiments, the contacting is performed in vitro. In some embodiments, the contacting is performed in vivo. In some embodiments, the method comprises modulating one or more cytokines selected from the group consisting of interleukin-6, interleukin-10, tumor necrosis factor-α, C-reactive protein, or any combination thereof, in the subject. In some embodiments, the methods provided herein further comprise identifying or having identified the subject as exhibiting abnormal expression of one or more cytokines. In some embodiments, the subject is identified or has been identified as exhibiting abnormal expression of interleukin-6, interleukin-10, tumor necrosis factor-α, C-reactive protein, or any combination thereof. In some embodiments, the cell or tissue is contacted with β-1,3/1,6-D-glucan.

In some embodiments, the methods provided herein further comprise modulating myosin in the subject, comprising contacting a cell or tissue associated with abnormal expression of myosin with β-1,3/1,6-D-glucan, or a pharmaceutically acceptable salt thereof.

In some embodiments, the methods provided herein further comprise modulating MDA, SOD, IL-6, hsCRP, TNF-α, Total Cholesterol, Triglycerides (TG), Low Density Lipids (LDL), High Density Lipids (HDL), fasting glucose, HbA1c, systolic BP, diastolic BP, the ratio of EPC-CEC, or any combination thereof, in the subject.

Combination Therapies

One or more additional therapeutic agents such as, for example, anti-inflammatory agents, steroids, immunosuppressants, anti-platelet aggregation agents, and anesthetics (e.g., for use in combination with a surgical procedure) or other agents useful for treating cardiac disorders (e.g., atherosclerosis, STEMI, and the like), hypertension, and diabetes (e.g., diabetes associated with heart disease), can be used in combination with the β-1,3/1,6-D-glucan described herein for treatment of the diseases provided herein. In some embodiments, one or more additional therapeutic agents are administered to the subject in combination with the polysaccharide comprising the β-1,3/1,6-D-glucan.

In some embodiments, the additional therapeutic agent(s) is administered simultaneously with the β-1,3/1,6-D-glucan provided herein. In some embodiments, the additional therapeutic agent is administered after administration of the β-1,3/1,6-D-glucan provided herein. In some embodiments, the additional therapeutic agent is administered prior to administration of the β-1,3/1,6-D-glucan provided herein.

In some embodiments, the additional therapeutic agent is administered simultaneously with the polysaccharide comprising the β-1,3/1,6-D-glucan provided herein. In some embodiments, the additional therapeutic agent is administered after administration of the polysaccharide comprising the β-1,3/1,6-D-glucan provided herein. In some embodiments, the additional therapeutic agent is administered prior to administration of the polysaccharide comprising the β-1,3/1,6-D-glucan provided herein.

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example steroids include, but are not limited to, corticosteroids such as cortisone, dexamethasone, hydrocortisone, methylprednisolone, prednisolone, and prednisone.

Example immunosuppressants include, but are not limited to, azathioprine, chlorambucil, cyclophosphamide, cyclosporine, daclizumab, infliximab, methotrexate, and tacrolimus.

Example agents for treating cardiac disorders include, but are not limited to, angiotensin-converting enzyme (ACE) inhibitors (e.g., enalapril, captopril), angiotensin II receptor blockers (e.g., losartan, valsartan), beta blockers (e.g., carvedilol, metoprolol, bisoprolol), diuretics (e.g., furosemide), aldosterone antagonists (e.g., spironolactone, eplerenone), and digoxin (i.e., *digitalis*). In some embodiments, the methods provided herein further comprise administering digoxin to the subject.

Example agents for treating hypertension include, but are not limited to, thiazide diuretics (e.g., hydrochlorothiazide, chlorthalidone), angiotensin-converting enzyme (ACE) inhibitors (e.g., enalapril, captopril), angiotensin II receptor blockers (e.g., losartan, valsartan), beta blockers (e.g., carvedilol, metoprolol, bisoprolol), calcium channel blockers (e.g., amlodipine, diltiazem), and renin inhibitors (e.g., aliskiren).

Example agents for treating diabetes include, but are not limited to, insulin, biguanidine agents (e.g., metformin, phenformin, and buformin), thiazolidinediones (e.g., pioglitazone), sulfonylureas (e.g., tolbutamide, acetohexamide, glipizide, glibenclamide, meglitinides (e.g., repaglinide, nateglinide), and alpha-glucosidase inhibitors (e.g., miglitol, acarbose, voglibose).

Example anesthetics include, but are not limited, to local anesthetics (e.g., lidocaine, procain, ropivacaine) and general anesthetics (e.g., desflurane, enflurane, halothane, isoflurane, methoxyflurane, nitrous oxide, sevoflurane, mmobarbital, methohexital, thiamylal, thiopental, diazepam, lorazepam, midazolam, etomidate, ketamine, propofol, alfentanil, fentanyl, remifentanil, buprenorphine, butorphanol, hydromorphone levorphanol, meperidine, methadone, morphine, nalbuphine, oxymorphone, pentazocine).

In some embodiments, the β-1,3/1,6-D-glucan is administered during a therapeutic procedure (e.g., a surgical procedure, administration of one or more additional therapeutic agents, and the like). In some embodiments, the β-1,3/1,6-D-glucan is administered in combination with an additional therapeutic agent during a therapeutic procedure.

In some embodiments, the β-1,3/1,6-D-glucan is administered from about 30 minutes to about 48 hours prior to a therapeutic procedure, for example, from about 30 minutes to about 48 hours, about 30 minutes to about 24 hours, about 30 minutes to about 12 hours, about 30 minutes to about 6 hours, about 30 minutes to about 2 hours, about 30 minutes to about 1 hour, about 1 hour to about 48 hours, about 1 hour to about 24 hours, about 1 hour to about 12 hours, about 1 hour to about 6 hours, about 1 hour to about 2 hours, about 2 hours to about 48 hours, about 2 hours to about 24 hours, about 2 hours to about 12 hours, about 2 hours to about 6 hours, about 6 hours to about 48 hours, about 6 hours to about 24 hours, about 6 hours to about 12 hours, about 12 hours to about 48 hours, about 12 hours to about 24 hours, or about 24 hours to about 48 hours.

In some embodiments, the β-1,3/1,6-D-glucan is administered from about 30 minutes to about 48 hours after a therapeutic procedure, for example, from about 30 minutes to about 48 hours, about 30 minutes to about 24 hours, about 30 minutes to about 12 hours, about 30 minutes to about 6 hours, about 30 minutes to about 2 hours, about 30 minutes to about 1 hour, about 1 hour to about 48 hours, about 1 hour to about 24 hours, about 1 hour to about 12 hours, about 1 hour to about 6 hours, about 1 hour to about 2 hours, about 2 hours to about 48 hours, about 2 hours to about 24 hours, about 2 hours to about 12 hours, about 2 hours to about 6 hours, about 6 hours to about 48 hours, about 6 hours to about 24 hours, about 6 hours to about 12 hours, about 12 hours to about 48 hours, about 12 hours to about 24 hours, or about 24 hours to about 48 hours.

Pharmaceutical Formulations and Formulations

When employed as pharmaceuticals, the β-1,3/1,6-D-glucan, or a pharmaceutically acceptable salt thereof, provided herein can be administered in the form of pharmaceutical compositions. In some embodiments, the β-1,3/1,6-D-glucan is administered in the form of a pharmaceutical composition. In some embodiments, the polysaccharide comprising the β-1,3/1,6-D-glucan is administered in the form of a pharmaceutical composition. These compositions can be prepared as described herein or elsewhere, and can be administered by a variety of routes, depending upon whether local or systemic treatment is desired and upon the area to be treated. In some embodiments, including without limitation for use in cosmetics, tonics, and health drinks, conventional pharmaceutical carriers, aqueous, powder or oily bases, thickeners and the like may be included. In some embodiments, the compositions provided herein are suitable for oral administration. In some embodiments, the compositions provided herein are suitable for parenteral administration. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump.

Also provided are pharmaceutical compositions which contain, as the active ingredient, the β-1,3/1,6-D-glucan provided herein in combination with one or more pharmaceutically acceptable carriers (e.g., excipients). Also provided are pharmaceutical compositions which contain, as the active ingredient, the polysaccharide comprising the β-1,3/

1,6-D-glucan provided herein in combination with one or more pharmaceutically acceptable carriers (e.g., excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, creams, jelly, emulsions, solutions, syrups, soft and hard gelatin capsules, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

Accordingly, the present application provides methods of treating a disease of the digestive system described herein in a subject in need thereof, comprising administering to the subject a pharmaceutical composition comprising β-1,3/1,6-D-glucan, or a pharmaceutically acceptable salt thereof, and one or more pharmaceutically acceptable excipients.

The present application further provides methods of treating one or more symptoms of a disease of the digestive system described herein in a subject in need thereof, comprising: a) identifying or having identified a subject as exhibiting one or more symptoms of the disease of the digestive system; and b) administering to the subject a pharmaceutical composition comprising β-1,3/1,6-D-glucan, or a pharmaceutically acceptable salt thereof, and one or more pharmaceutically acceptable excipients. In some embodiments, at least one of the symptoms is inflammation associated with the disease of the digestive system.

In some embodiments, the subject is identified or has been identified as exhibiting inflammation associated with a disease of the digestive system. In some embodiments, the subject is identified or has been identified as exhibiting inflammation associated with one or more organs of the digestive system. In some embodiments, the subject is identified or has been identified as exhibiting inflammation associated with one or more organs associated with the digestive system. In some embodiments, the subject is identified or has been identified as exhibiting one or more symptoms associated with a disease of the digestive system selected from the group consisting of inflammatory bowel disease, Crohn's disease, and ulcerative colitis.

The present application further provides methods of treating ST-elevation myocardial infarction in a subject in need thereof, comprising administering to the subject a pharmaceutical composition comprising β-1,3/1,6-D-glucan, or a pharmaceutically acceptable salt thereof, and one or more pharmaceutically acceptable excipients.

The present application further provides methods of treating one or more symptoms of ST-elevation myocardial infarction in a subject in need thereof, comprising: a) identifying or having identified a subject as exhibiting one or more symptoms of the ST-elevation myocardial infarction; and b) administering to the subject a pharmaceutical composition comprising β-1,3/1,6-D-glucan, or a pharmaceutically acceptable salt thereof, and one or more pharmaceutically acceptable excipients. In some embodiments, at least one of the symptoms is inflammation associated with ST-elevation myocardial infarction.

In some embodiments, the pharmaceutical composition comprises about 10 mg to about 1 g β-1,3/1,6-D-glucan, or a pharmaceutically acceptable salt thereof, for example, about 10 mg to about 1 g, about 10 mg to about 800 mg, about 10 mg to about 600 mg, about 10 mg to about 400 mg, about 10 mg to about 200 mg, about 10 mg to about 100 mg, about 10 mg to about 50 mg, about 50 mg to about 1 g, about 50 mg to about 800 mg, about 50 mg to about 600 mg, about 50 mg to about 400 mg, about 50 mg to about 200 mg, about 50 mg to about 100 mg, about 100 mg to about 1 g, about 100 mg to about 800 mg, about 100 mg to about 600 mg, about 100 mg to about 400 mg, about 100 mg to about 200 mg, about 200 mg to about 1 g, about 200 mg to about 800 mg, about 200 mg to about 600 mg, about 200 mg to about 400 mg, about 400 mg to about 1 g, about 400 mg to about 800 mg, about 400 mg to about 600 mg, about 600 mg to about 1 g, about 600 mg to about 800 mg, or about 800 mg to about 1 g. In some embodiments, the pharmaceutical composition comprises about 500 mg to about 600 mg β-1,3/1,6-D-glucan, or a pharmaceutically acceptable salt thereof. In some embodiments, the pharmaceutical composition comprises about 500 mg to about 550 mg β-1,3/1,6-D-glucan, or a pharmaceutically acceptable salt thereof.

The present application further provides methods of treating inflammatory bowel disease in a subject in need thereof, comprising administering to the subject a pharmaceutical composition comprising about 500 mg to about 600 mg of β-1,3/1,6-D-glucan, or a pharmaceutically acceptable salt thereof, and one or more pharmaceutically acceptable excipients.

The present application further provides methods of treating Crohn's disease in a subject in need thereof, comprising administering to the subject a pharmaceutical composition comprising about 500 mg to about 600 mg of β-1,3/1,6-D-glucan, or a pharmaceutically acceptable salt thereof, and one or more pharmaceutically acceptable excipients. In some embodiments, β-1,3/1,6-D-glucan is administered to the subject.

The present application further provides methods of treating ulcerative colitis in a subject in need thereof, comprising administering to the subject a pharmaceutical composition comprising about 500 mg to about 600 mg of β-1,3/1,6-D-glucan, or a pharmaceutically acceptable salt thereof, and one or more pharmaceutically acceptable excipients.

In some embodiments, the pharmaceutical composition comprises β-1,3/1,6-D-glucan. In some embodiment, the pharmaceutical composition comprises the polysaccharide comprising the β-1,3/1,6-D-glucan provided herein.

Definitions

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "subject" or "patient," used interchangeably, refers to any animal, including mammals, preferably mice, rats, other rodents, rabbits, dogs, cats, swine, cattle, sheep, horses, or primates, and most preferably humans.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

As used herein, the term "contacting" refers to the bringing together of indicated moieties in an in vitro system or an in vivo system. For example, "contacting" one or more cytokines with the β-1,3/1,6-D-glucan described herein includes the administration of the β-1,3/1,6-D-glucan to an individual or subject, such as a human, having one or more of the cytokines described herein, as well as, for example, introducing β-1,3/1,6-D-glucan into a sample containing a cellular or purified preparation containing one or more cytokines.

As used herein, "pharmaceutically acceptable salts" refers to derivatives of the disclosed compounds (e.g., β-1,3/1,6-D-glucan or the polysaccharide comprising the 0-1,3/1,6-D-glucan) wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media such as diethyl ether, ethyl acetate, alcohols (e.g., methanol, ethanol, isopropanol, or butanol), or acetonitrile are preferred. Lists of suitable salts can be found, for example, in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Example 1. Analysis of Polysaccharide Derived from *Ganoderma lucidum* Mycelium

The polysaccharide derived from *Ganoderma lucidum* was analyzed according to the following methods:
Glycosyl Composition by GC-MS of TMS Derivatives of Methyl Glycosides Glycosyl composition analysis was performed by combined gas chromatography/mass spectrometry (GC/MS) of the per-O-trimethylsilyl (TMS) derivatives of the monosaccharide methyl glycosides produced from the sample by acidic methanolysis as described previously by Santander et al. Microbiology, 2013, 159:1471.
Glycosyl Linkage Analysis For glycosyl linkage analysis, the samples were permethylated, depolymerized, reduced, and acetylated; and the resultant partially methylated alditol acetates (PMAAs) analyzed by gas chromatography-mass spectrometry (GC-MS) as described by Heiss et al. *Carbohydr. Res.* 2009, 344:915.
Size-Exclusion Chromatography (SEC)

Figure 2A:
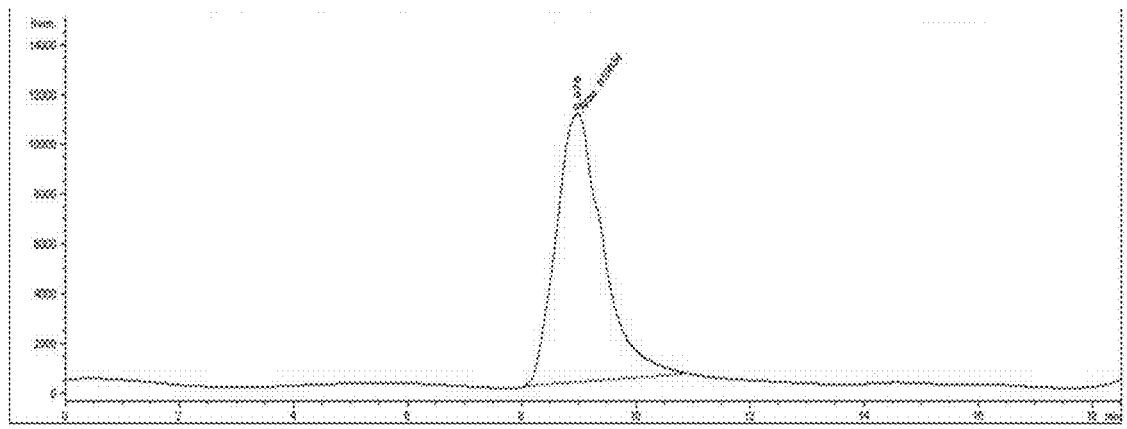
FIGS. 2A-2B show a representative size exclusion chromatograph profile of the polysaccharide isolated from *Ganoderma lucidum* mycelium, comprising β-1,3/1,6-D-glucan.
Figure 2B:
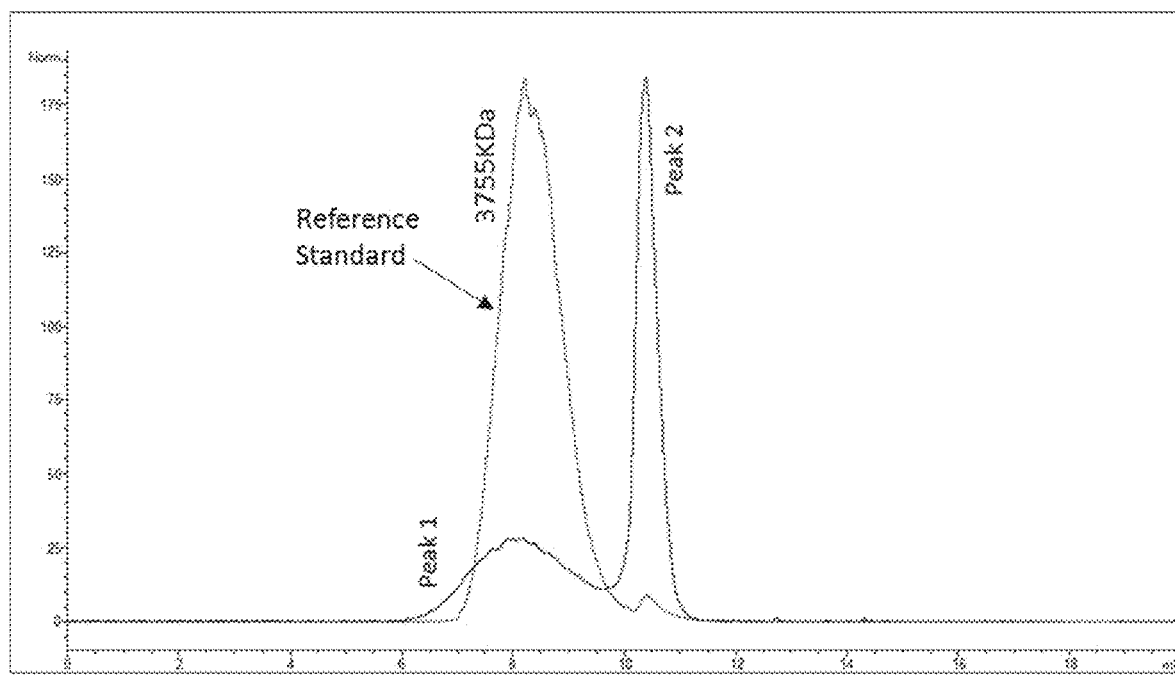

The intact sample was loaded onto Superose12 GE-Amersham with optimal separation range 1000-167,000 Da for dextrans, and the high MW fraction was collected as "Peak 1" (i.e., Pk1) and was further analyzed for glycosyl composition and linkage analysis, and by 1D NMR-spectroscopy. A representative SEC profile, as shown in FIG. 2A, shows that the polysaccharide containing Peak 1 eluted at 8.9 min. Fractions were collected between 7 and 12 min via multiple runs to isolate several mg of the polysaccharide. The obtained material was washed with nanopure water and freeze dried for several times to remove any remaining buffer residues. From SEC measurements, the molecular weight of Pk1 was found to be approximately 3,800-4,000 kDa, as shown in FIG. 2B. The molecular weight reference standard used for the SEC molecular weight measurement was 3,755 kDa. A second peak (Peak 2) was found to have a molecular weight of less than 5,000 Da, as shown in FIG. 2B and below in Table 1A.

TABLE 1A

| Peak | Average Molecular Weight (Da) | Peak area % |
|---|---|---|
| Peak 1 | >3,755,000 | 54 |
| Peak 2 | <5,000 | 46 |

Tip-Sonication

To dissociate the polysaccharide Pk1 and to improve solubility, tip sonication was applied using Sonic Dismembrator 550 (Fisher Scientific) with micro tip.
NAMR-spectroscopy The Peak 1 sample (~5 mg) was deuterium-exchanged by lyophilization in $D_2O$. The total amount of the Peak 1 sample was dissolved in 0.6 mL DMSO-$d_6$ by incubating in 100° C. degree heat block for 1 h. $D_2O$ (100 μL), was added to the solution and the solution was transferred into a 5 mm OD NMR tube. 1D-Proton NMR of the sample in DMSO-$d_6$ and $D_2O$ (6:1) was acquired on a 600 MHz Varian Inova instrument at 65° C. Chemical shifts were referenced to TMS (0 ppm).

Figure 3:
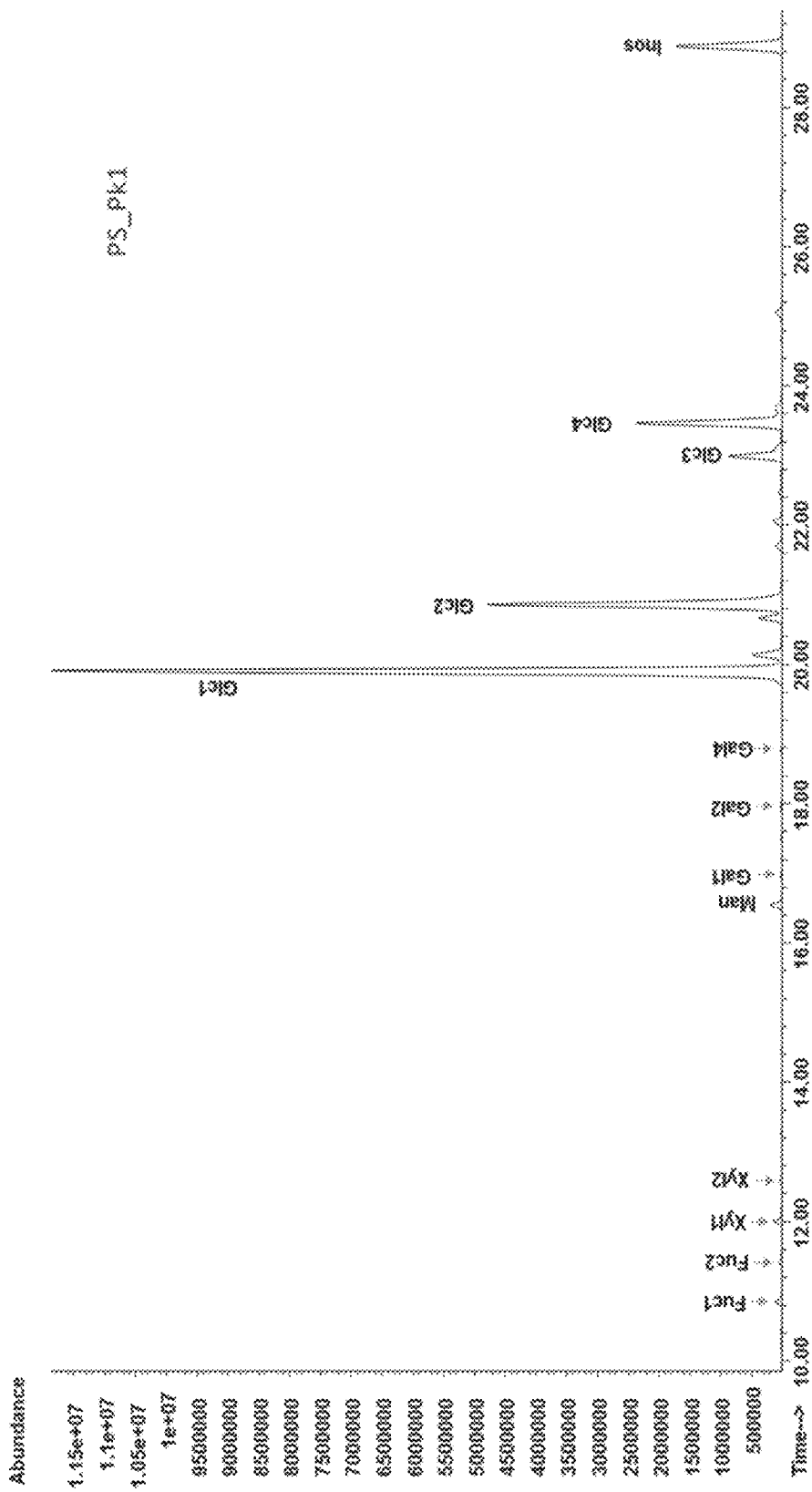
FIG. 3 shows the glycosyl composition analysis of the polysaccharide comprising β-1,3/1,6-D-glucan isolated from *Ganoderma lucidum* mycelium.

Glycosyl composition analysis of the Peak 1 sample indicated that Glucose (Glc) was the main residue at ~97.4 mol %. Fuc, Gal, Xyl and Man were detected in minor amounts as shown in FIG. 3 and below in Table 1B. Total carbohydrate weight percent was 75.8% as determined by composition analysis.

TABLE 1B

Glycosyl Composition Analysis of the Peak 1 Sample

| Glycosyl residue | Mass (μg) | Mol %[1] |
|---|---|---|
| Ribose (Rib) | n.d. | — |
| Arabinose (Ara) | n.d. | — |
| Rhamnose (Rha) | n.d. | — |
| Fucose (Fuc) | 1.8 | 0.6 |
| Xylose (Xyl) | 2.5 | 0.9 |
| Glucuronic Acid (GlcA) | n.d. | — |
| Galacturonic acid (GalA) | n.d. | — |
| Mannose (Man) | 3.1 | 1.0 |
| Galactose (Gal) | 1.2 | 0.4 |
| Glucose (Glc) | 317.2 | 97.2 |
| N-Acetyl Galactosamine (GalNAc) | n.d. | — |
| N-Acetyl Glucosamine (GlcNAc) | n.d. | — |
| N-Acetyl Mannosamine (ManNAc) | n.d. | — |
| Σ = | 325.9 | 100.1 |

[1]Values are expressed as mole percent of total carbohydrate;
n.d.—not detected
The total mol percentage may not add to exactly 100% due to rounding.

Figure 4:
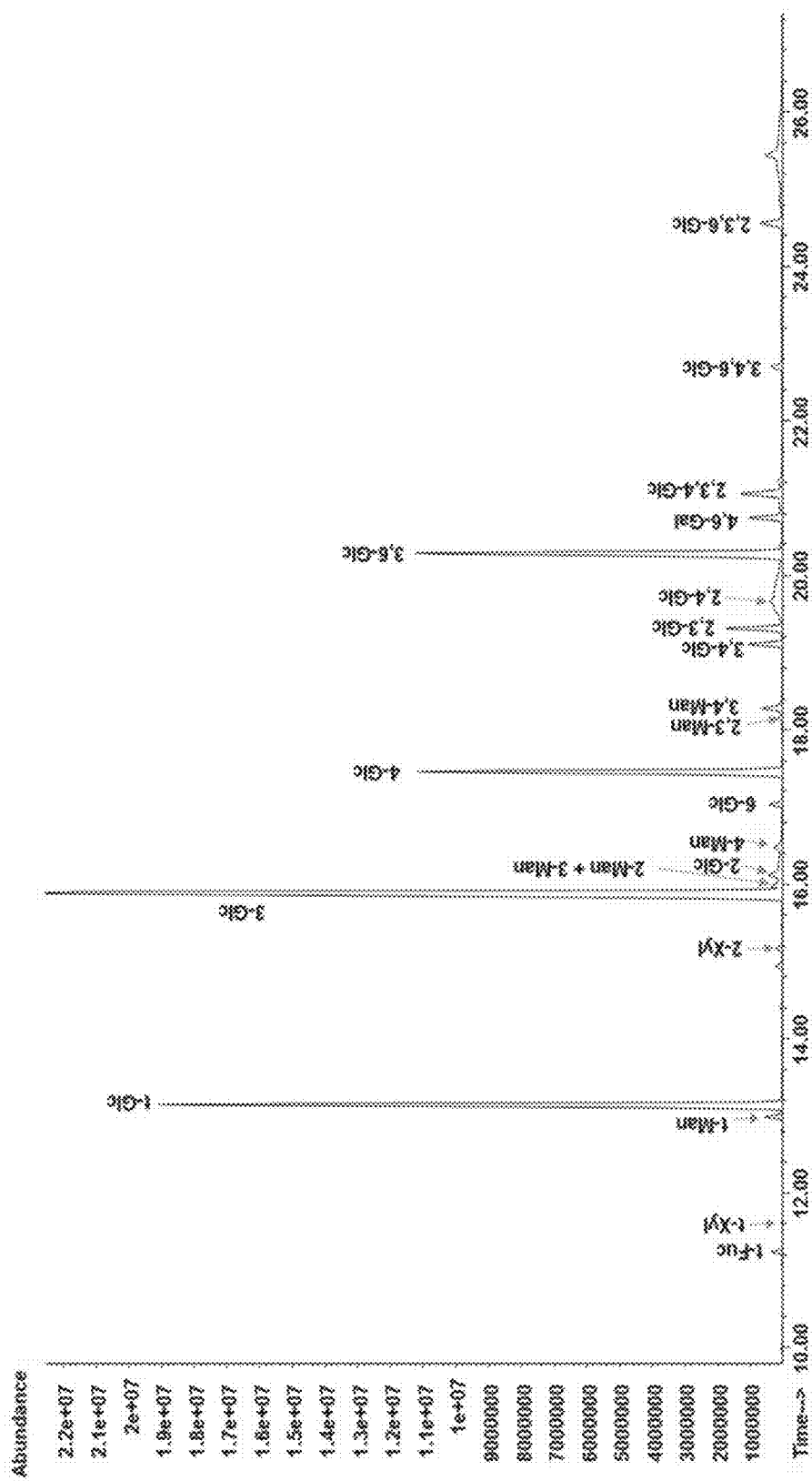
FIG. 4 shows the glycosyl linkage analysis of the polysaccharide comprising β-1,3/1,6-D-glucan isolated from *Ganoderma lucidum* mycelium.

Results of the glycosyl linkage analysis of the Peak 1 sample indicated the presence of variously linked glucosyl residues, as shown in FIG. 4 and below in Table 2.

TABLE 2

Glycosyl Linkage Analysis of Peak 1 Sample

| Residue | Retention Time | Peak Area | Area % |
|---|---|---|---|
| Terminal Fucopyranosyl residue (t-Fuc) | 11.241 | 8435724 | 0.3 |
| Terminal Xylopyranosyl residue (t-Xyl) | 11.613 | 892156 | 0.0 |
| Terminal Mannopyranosyl residue (t-Man) | 12.99 | 14055056 | 0.6 |
| Terminal Glucopyranosyl residue (t-Glc) | 13.15 | 551956030 | 22.9 |
| 2 linked Xylopyranosyl residue (2-Xyl) | 15.166 | 6070200 | 0.3 |
| 3 linked Glucopyranosyl residue (3-Glc) | 15.888 | 829730729 | 34.4 |
| 2 linked Mannopyranosyl residue (2-Man) | 15.976 | 10988548 | 0.5 |
| 3 linked Mannopyranosyl residue (3-Man) | 15.976 | 10988548 | 0.5 |
| 2 linked Glucopyranosyl residue (2-Glc) | 16.115 | 15972737 | 0.7 |
| 4 linked Mannopyranosyl residue (4-Man) | 16.472 | 9248469 | 0.4 |
| 6 linked Glucopyranosyl residue (6-Glc) | 17.027 | 11464752 | 0.5 |
| 4 linked Glucopyranosyl residue (4-Glc) | 17.451 | 342058583 | 14.2 |
| 2,3 linked Mannopyranosyl residue (2,3-Man) | 18.146 | 2502773 | 0.1 |
| 3,4 linked Mannopyranosyl residue (3,4-Man) | 18.273 | 17648317 | 0.7 |
| 3,4 linked Glucopyranosyl residue (3,4-Glc) | 19.103 | 30574742 | 1.3 |
| 2,3 linked Glucopyranosyl residue (2,3-Glc) | 19.307 | 50623330 | 2.1 |
| 2,4 linked Glucopyranosyl residue (2,4-Glc) | 19.656 | 12432266 | 0.5 |
| 3,6 linked Glucopyranosyl residue (3,6-Glc) | 20.281 | 379093860 | 15.7 |
| 4,6 linked Galactopyranosyl residue (4,6-Gal) | 20.74 | 28991113 | 1.2 |
| 2,3,4 linked Glucopyranosyl residue (2,3,4-Glc) | 21.051 | 41995625 | 1.7 |
| 3,4,6 linked Glucopyranosyl (3,4,6-Glc) | 22.694 | 11627484 | 0.5 |
| 2,3,6 linked Glucopyranosyl residue (2,3,6-Glc) | 24.554 | 24101514 | 1.0 |
| Total | | 2411452556 | 100 |

Linkage results of the Peak 1 sample (Table 2) indicated the presence of variously linked glucosyl residues. The major linkages identified were: t-Glc (22.9% of total peak area), 3-Glc (34.4% of total peak area), 4-Glc (>14.2% of total peak area) and 3,6-Glc (15.7% of total peak area) were detected. Furthermore, variously linked Man, Gal, Fuc, and Xyl residues were detected. The data corresponded with the results received from glycosyl composition analyses. The glycosyl composition results were calculated as mol % whereas linkage analysis results were calculated as peak area. According to the results of linkage analysis, the total percentage of 3-Glc and 3,6-Glc together was approximately 76% of the total peak area. The linkage data in Table 2 also indicated that the ratio of 3-linked glucan (34.4%) to 3,6-Glc (15.7%) is 2:1.

Figure 5:
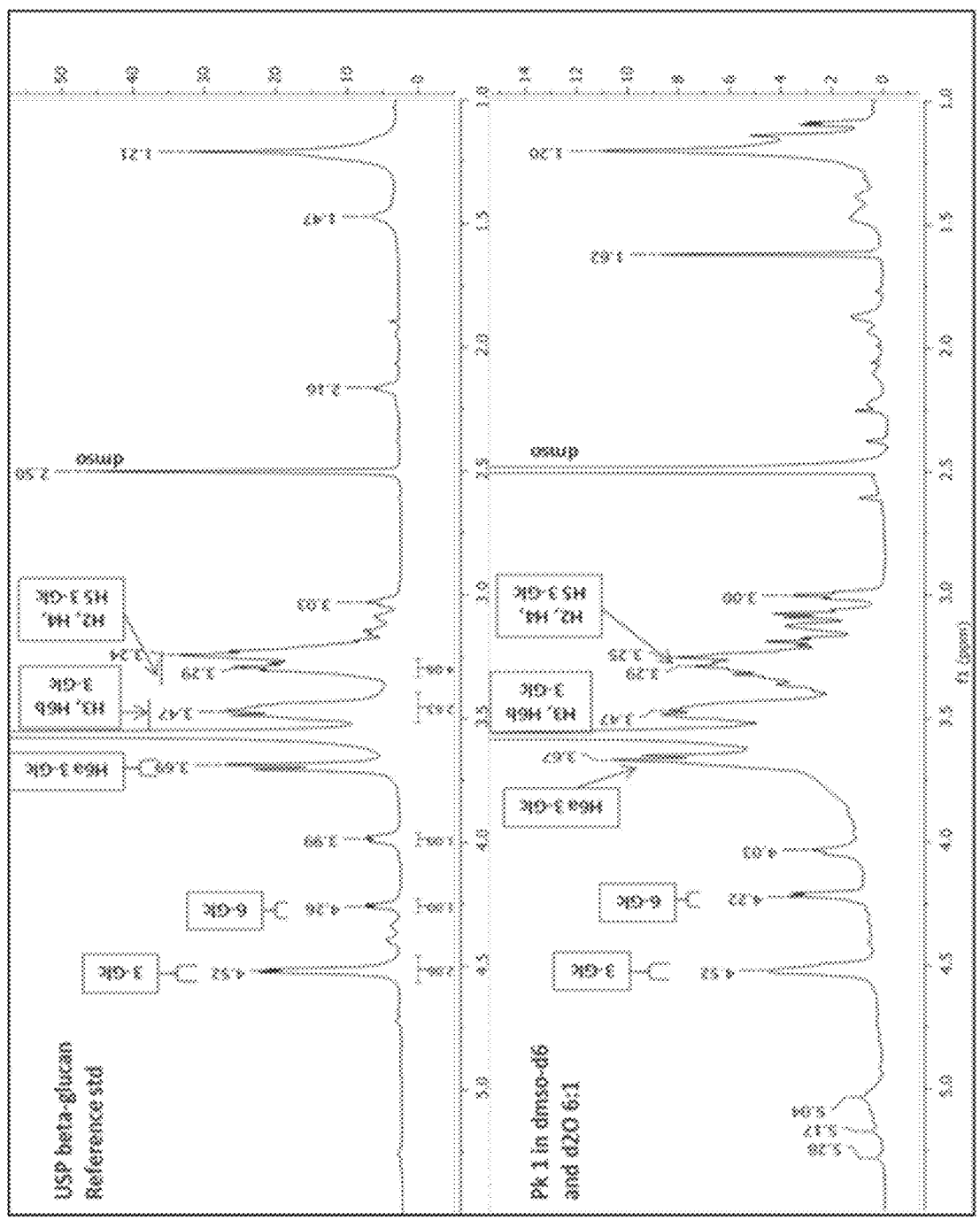
FIG. 5 shows 1D-Proton NMR spectrum of the Pk 1 sample in DMSO-$d_6$:$D_2O$ (6:1 mixture).
Figure 6A:
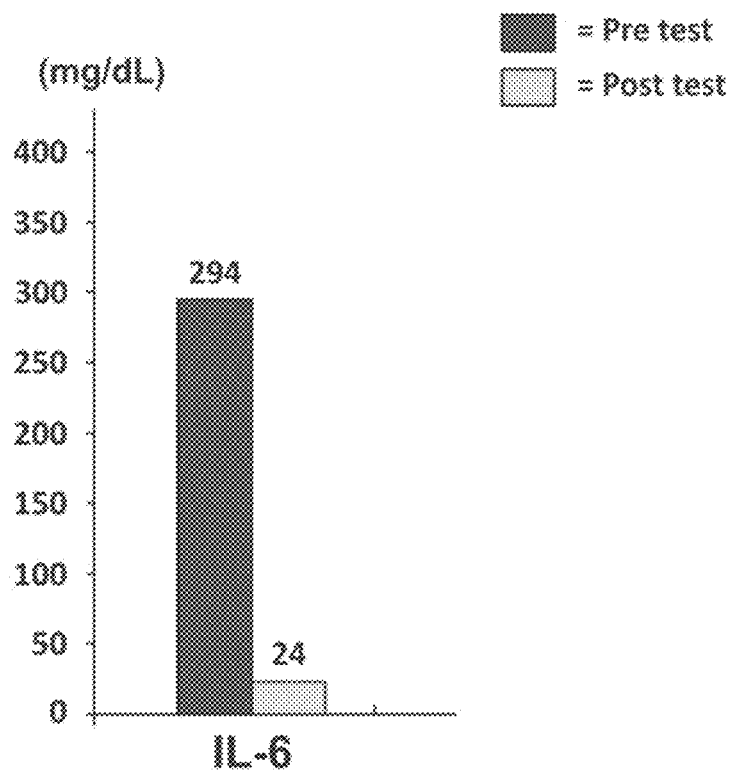
FIG. 6A-6B shows the effect of β-1,3/1,6-D-glucan administration on the level of inflammatory parameters Interleukin-6 (IL-6) (FIG. 6A), tumor necrosis factor-α (TNF-α) and high-sensitive C-reactive protein (hs-CRP) (FIG. 6B) in patients with stable angina pectoris (SAP).
Figure 6B:
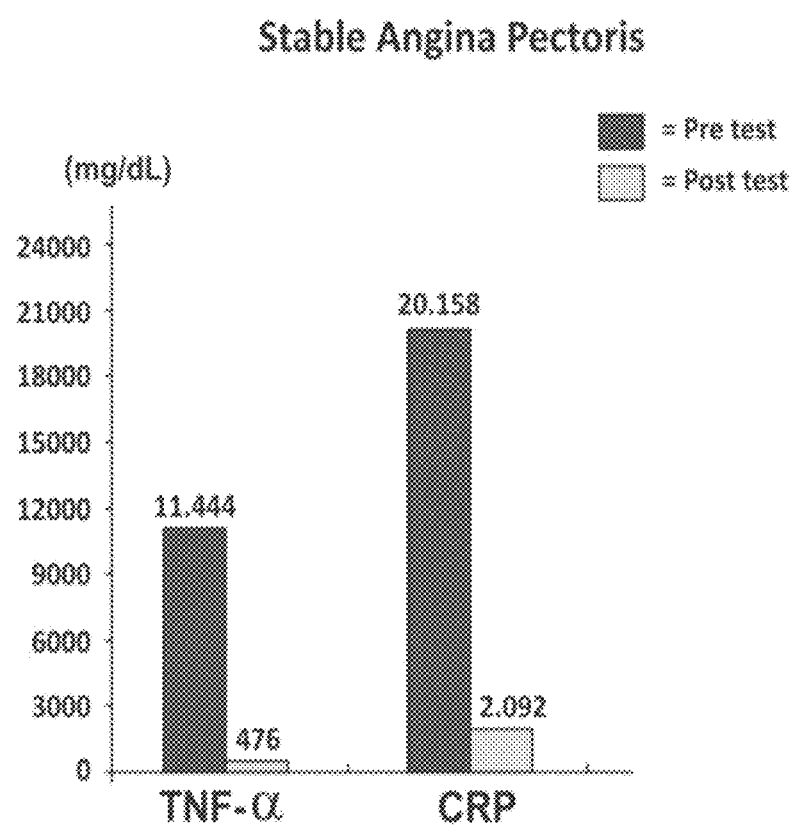
Figure 7:
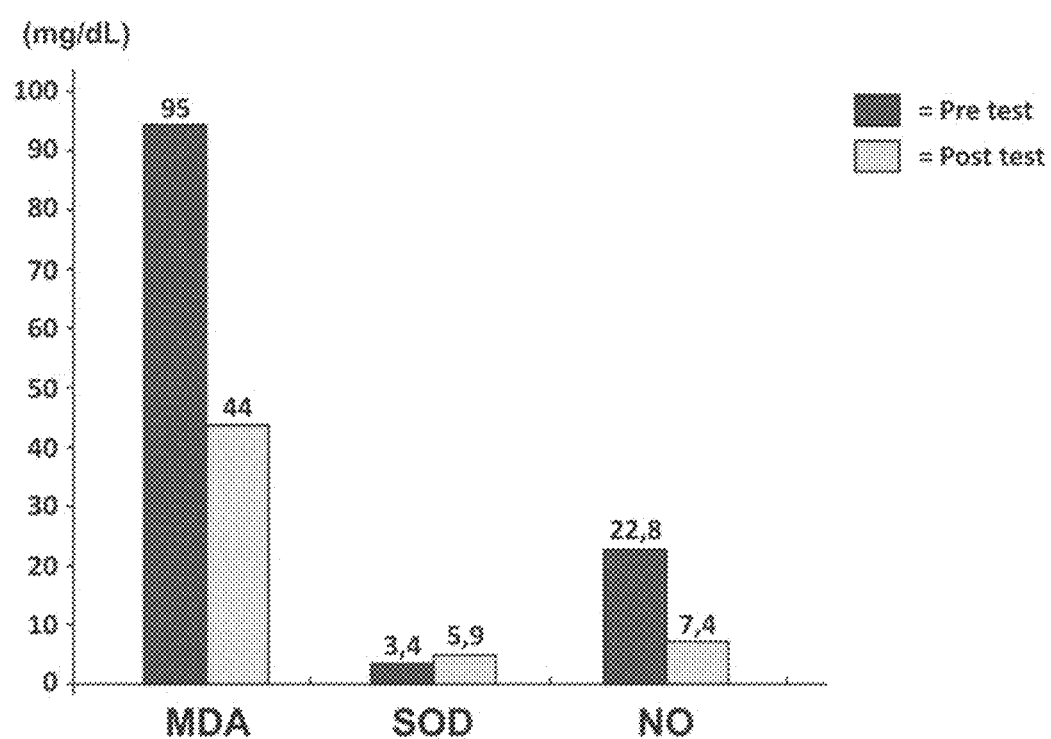
FIG. 7 shows the effect of β-1,3/1,6-D-glucan administration on MDA, SOD and NO levels in patients with stable angina pectoris (SAP).
Figure 8:
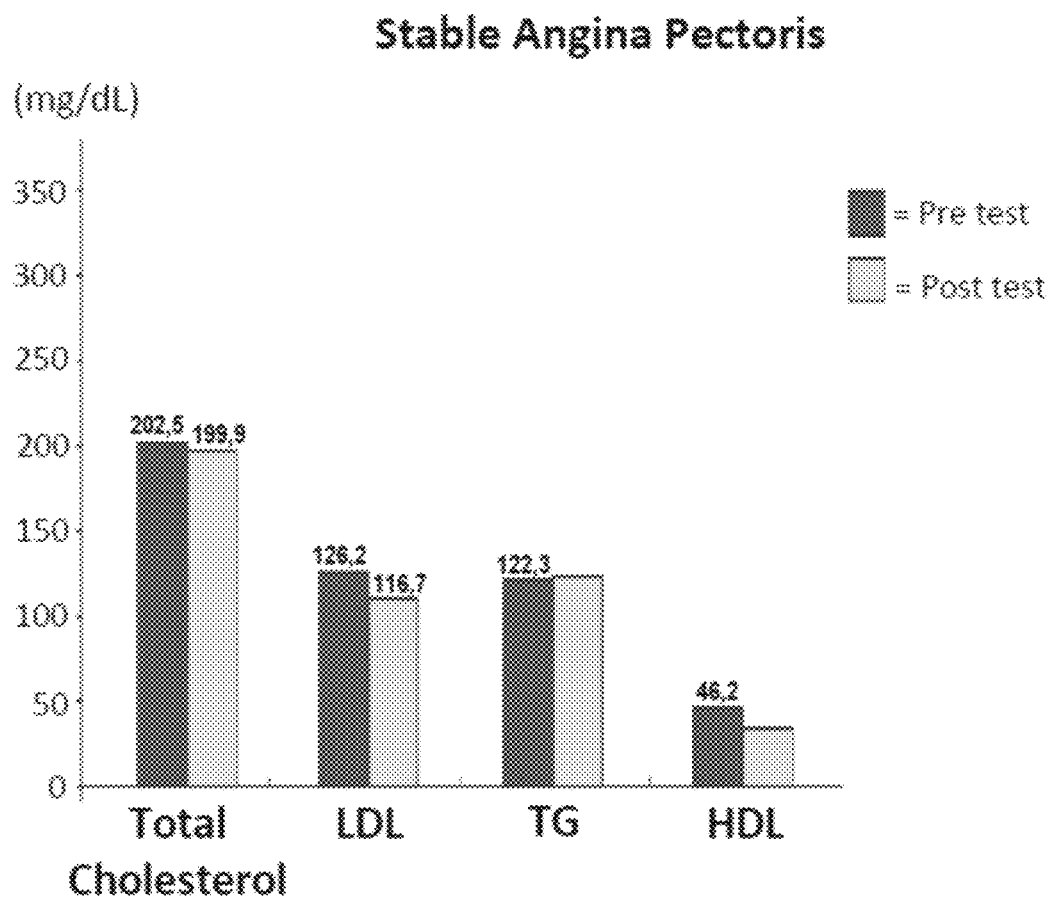
FIG. 8 shows the effect of β-1,3/1,6-D-glucan administration on total cholesterol, low-density lipid (LDL), triglyceride (TG), and high-density lipid (HDL) levels in patients with stable angina pectoris (SAP).
Figure 9:
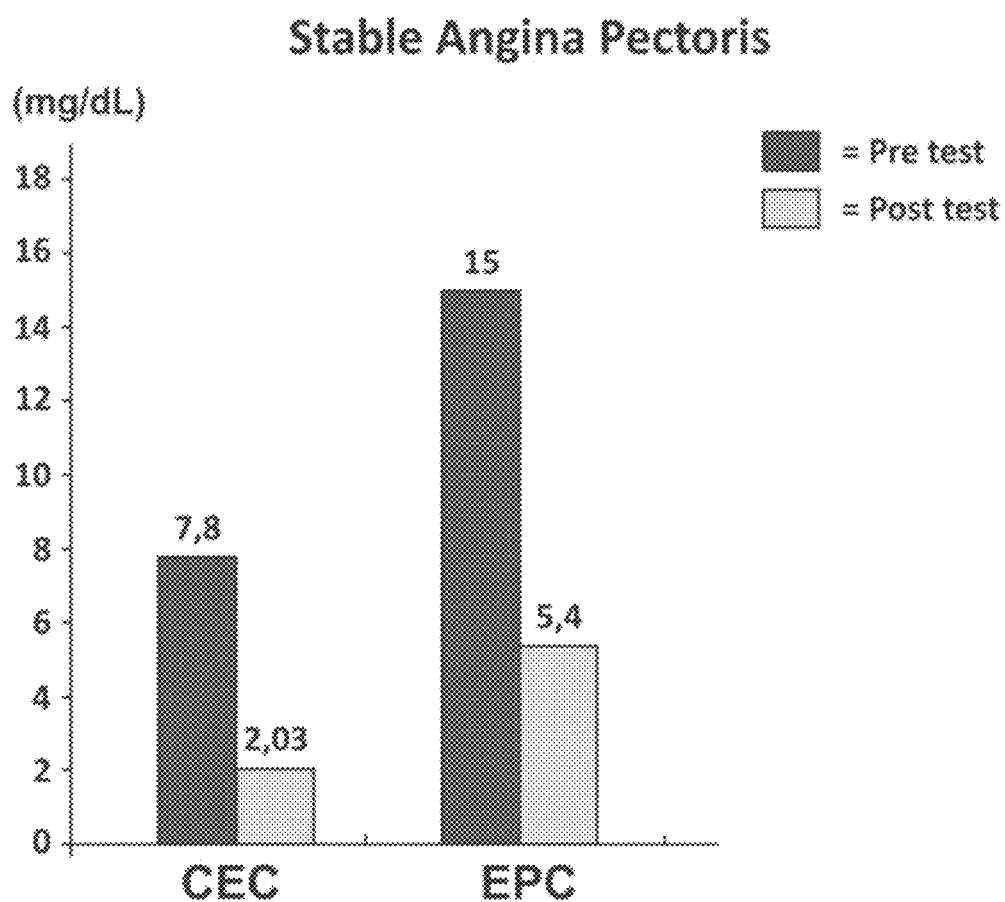
FIG. 9 shows the effect of β-1,3/1,6-D-glucan administration on the level of endothelial dysfunction parameters, circulating endothelial cell (CEC) and endothelial progenitor cell (EPC) in patients with stable angina pectoris (SAP).
Figure 10:
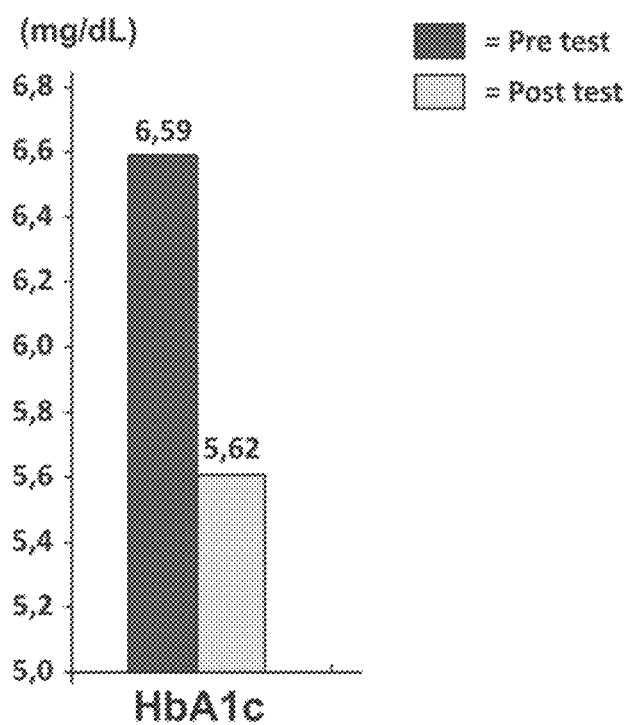
FIG. 10 shows the effect of β-1,3/1,6-D-glucan administration on HbA1c levels in patients with stable angina pectoris (SAP).
Figure 11A:
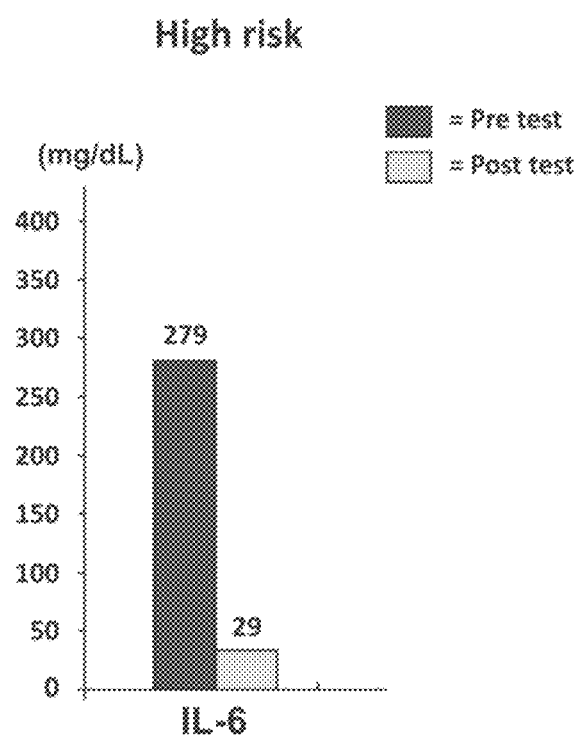
FIG. 11A-11B shows the effect of β-1,3/1,6-D-glucan administration on the level of inflammatory parameters Interleukin-6 (IL-6) (FIG. 11A), tumor necrosis factor-α (TNF-α) and high-sensitive C-reactive protein (hs-CRP) (FIG. 11B) in high risk patients.
Figure 11B:
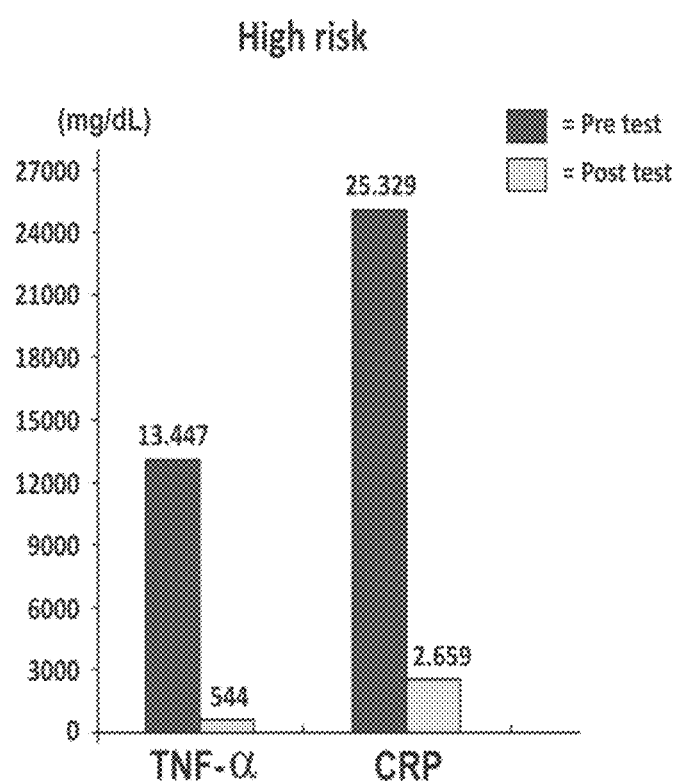
Figure 12:
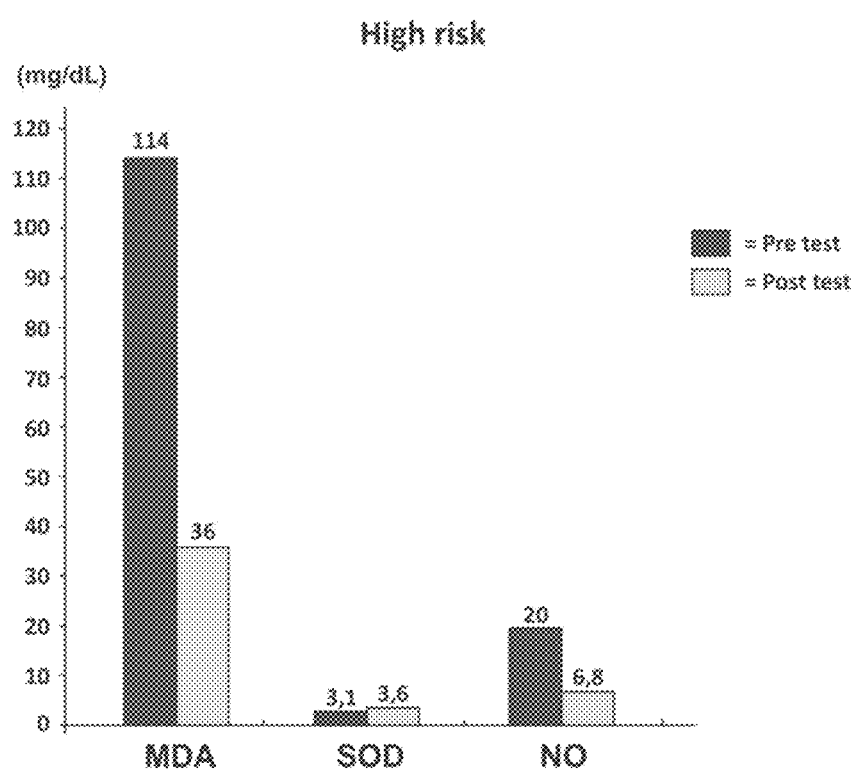
FIG. 12 shows the effect of β-1,3/1,6-D-glucan administration on MDA, SOD and NO levels in high risk patients.
Figure 13:
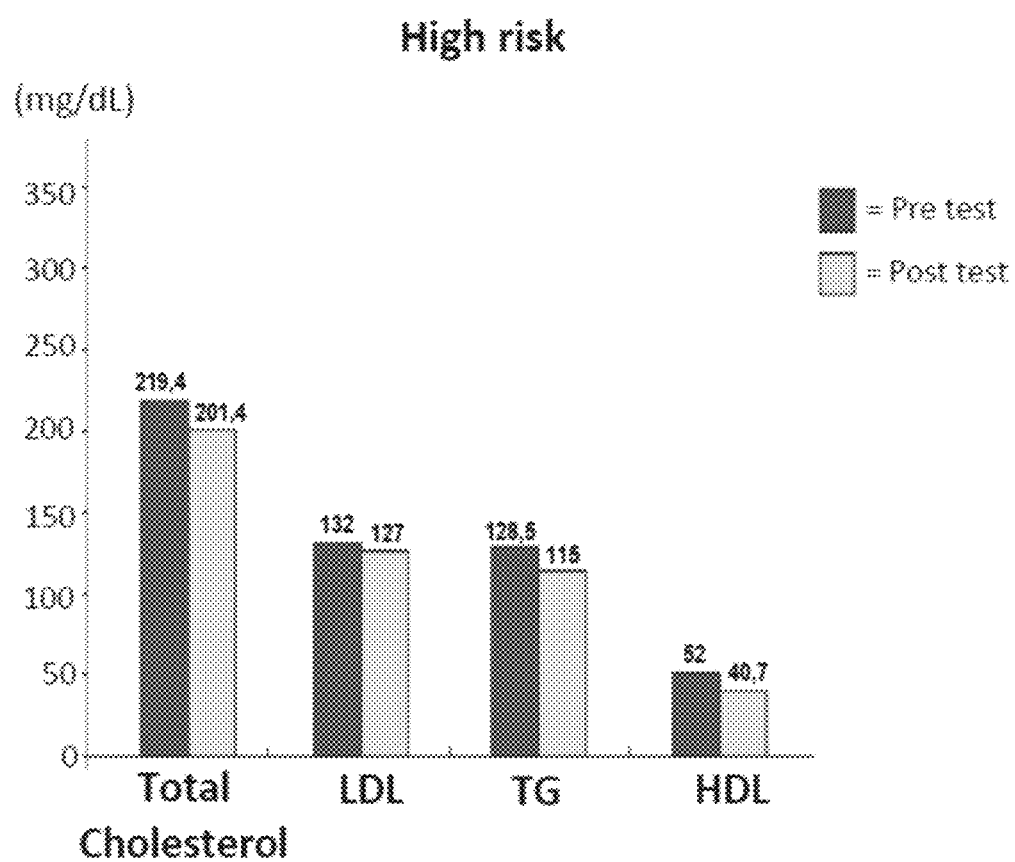
FIG. 13 shows the effect of β-1,3/1,6-D-glucan administration on total cholesterol, low-density lipid (LDL), triglyceride (TG), and high-density lipid (HDL) levels in high risk patients.
Figure 14:
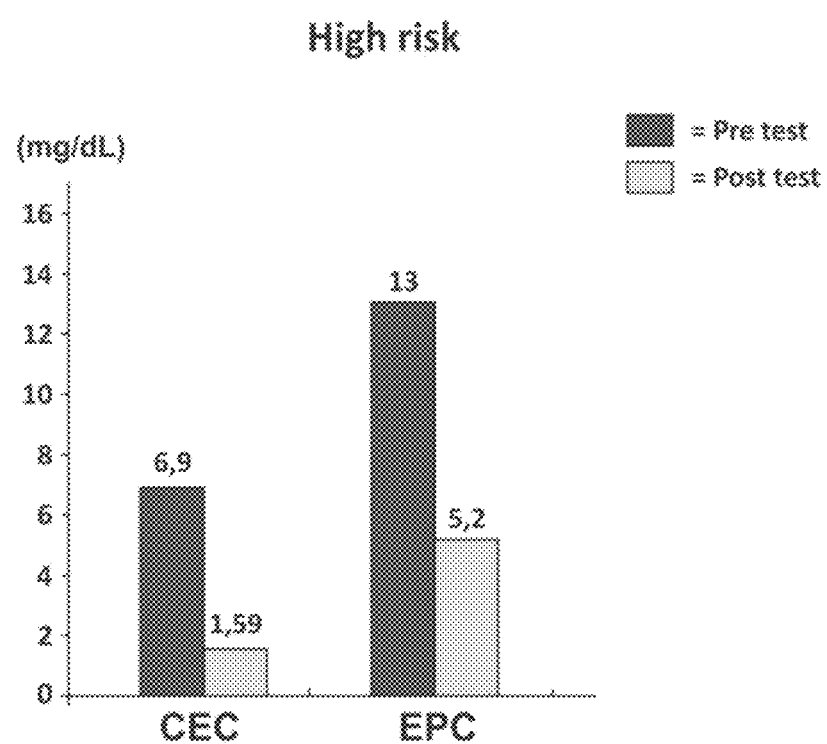
FIG. 14 shows the effect of β-1,3/1,6-D-glucan administration on the level of endothelial dysfunction parameters, circulating endothelial cell (CEC) and endothelial progenitor cell (EPC) in high risk patients.
Figure 15:
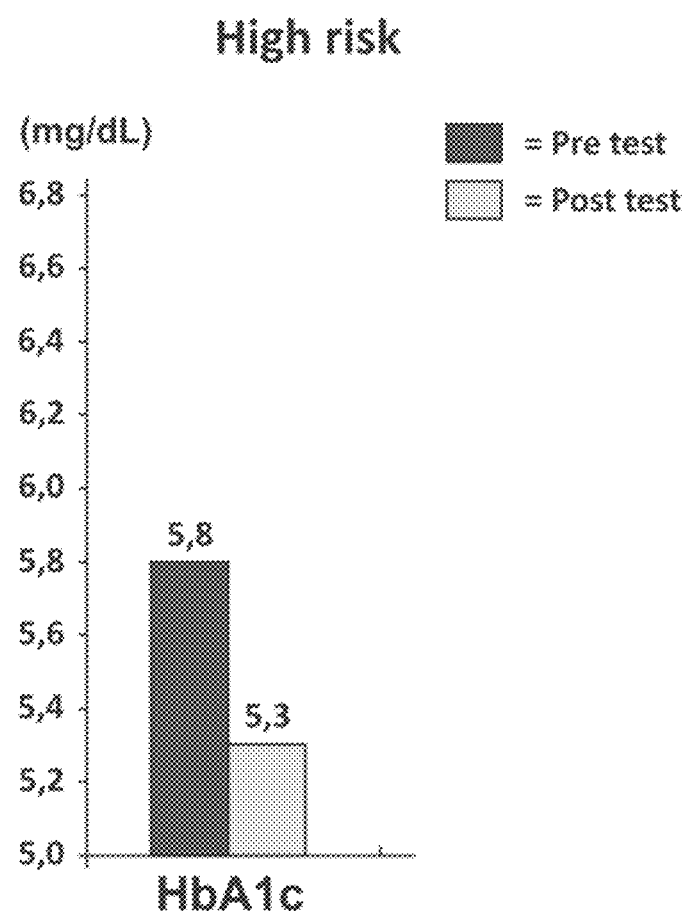
FIG. 15 shows the effect of β-1,3/1,6-D-glucan administration on HbA1c levels in high risk patients.

The Peak 1 sample (i.e., Pk 1) isolated by preparative SEC was analyzed by 1D NMR spectroscopy, as shown in FIG. 5. 1D-Proton NMR-spectroscopic profile of the Pk 1 in DMSO (DMSO-$d_6$ and $D_2O$ 6:1 mixture) correlated to the proton NMR profile of the β-Glucan USP (USP reference standard for β-glucan) confirming that the main component of the Pk1 sample was β-1,3/1,6-glucan. Based on the combined linkage data and 1D-Proton NMR data in dmso-$d_6$ the ratio between the 3-linked and 3,6-linked beta-glucan is 2:1 (Reference Standard: U.S. Pharmacopeia beta-glucan reference standard, Catalog Number 1048288, Lot FOK129).

TABLE 3

Integral values of the beta-glucan anomers of Pk 1
1D Proton NMR in DMSO-$d_6$

| Peak, δ ppm | Residue | Normalized |
|---|---|---|
| 4.57 | 3-β-Glc | 2.06 |
| 4.25 | 6-β-Glc | 1.00 |

Based on these data, the structure of the beta-glucan was determined and is shown below:

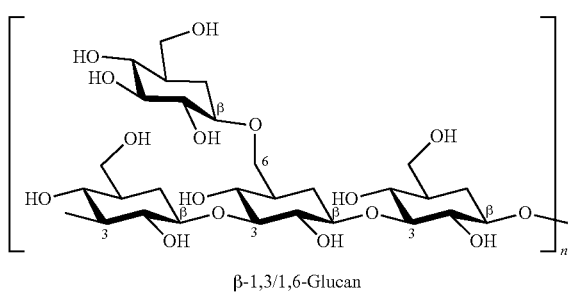

β-1,3/1,6-Glucan

Glucan Content

The total glucan content in the polysaccharide was measured using a mushroom and yeast β-glucan assay kit (Megazyme). Table 4 shows representative analysis data of the total glucan content in batches of the polysaccharide derived from mycelium of *Ganoderma lucidum*.

TABLE 4

| Batch Number | Total-glucan (%) | α-glucan (%) | β-glucan (%) |
| --- | --- | --- | --- |
| 1 | 55.73 | 0.27 | 55.46 |
| 2 | 53.66 | 0.27 | 53.39 |
| 3 | 53.40 | 0.66 | 52.74 |
| 4 | 55.36 | 0.95 | 54.41 |
| 5 | 51.08 | 0.03 | 51.05 |
| 6 | 57.46 | 0.31 | 57.15 |
| 7 | 56.40 | 0.41 | 55.99 |
| 8 | 52.82 | 0.32 | 52.50 |
| 9 | 53.49 | 0.84 | 52.65 |
| 10 | 50.85 | 0.54 | 50.31 |

Example 2. Treatment of Atherosclerosis Using β-1,3/1,6-D-Glucan

This study was conducted to determine the effect of β-1,3/1,6-D-glucan in inhibiting the formation of atherosclerosis in patients with stable angina pectoris (SAP) and high risk patients (according to the Framingham score). To study the difference between the pre-test and post-test treatment of 2 groups of patients (high-risk and (SAP)), a divergence test was performed using paired t test. An analysis was also performed by comparing the equal treatment of the different yields between the test groups. The two groups of patients were classified according to the criteria described below:

Stable Angina Pectoris: Patients who experience typical angina complaints, such as discomfort in the chest area with substernal crescendo characteristics that lasts approximately 10-15 minutes and is provoked by emotional stress activity that disappear after rest or nitroglycerin administration, with ST-T wave change either ST segment depression of 0.5 mm or inverted T of 1 mm.

High Risk Patients/High Risk: The risk of coronary heart disease categorization for the next 10 years using a predictor of age, diabetes mellitus, smoking, blood pressure, total cholesterol level, HDL and LDL cholesterol using Framingham Score. Risk factor stratification for coronary heart disease is declared high risk >20% according to ATP panel III.

The present study has previously shown that β-1,3/1,6-D-glucan significantly reduces the levels of MDA, hs-CRP, H2O2, total cholesterol, and foam cells, and increase levels of HDL in experimental animals (Wistar strain *Rattus novergicus*) given a high-fat diet. The β-1,3/1,6-D-glucan also reduced the level of LDL, triglyceride, TNF-α and IL-6. The β-1,3/1,6-D-glucan, an anti-oxidant and anti-inflammatory agent, is effective in reducing chronic inflammatory processes and oxidative stress that occur in the pathogenesis of cardiovascular disease. The present study further demonstrated that no toxic effects were found in both acute and subchronic studies on the administration of β-1,3/1,6-D-glucan to the experimental animals in any of the brain, kidney, liver, and lungs. The inhibition mechanism of the formation of atherosclerosis was identified by measuring the following parameters in the patient test groups: MDA, SOD, IL-6, hsCRP, TNF-α, Total Cholesterol, Triglycerides, Low Density Lipids (LDL), High Density Lipids (HDL), fasting glucose, HbA1c, systolic BP, diastolic BP and the ratio of EPC-CEC.

Measurement of lipid profiles, IL-6, hsCRP, MDA, and SOD were performed using human blood with pre-test and post-test treated blood collection. Measurement of lipid profile (HDL, LDL, triglycerides and total cholesterol) was performed with a colorimetric spectrophotometry test using Cobasmira tool. Measurement of IL-1, TNF Alpha, IL-6, hsCRP, MDA, SOD, CEC, NO, EPC, leptin and adiponectin was performed using an ELISA kit.

Data is presented in ±Standard Deviation (SD) mean form. To measure the difference between the 2 groups of patients with High-Risk and SAP pre-test and post-test treatment, a divergence test was performed using paired t test. If the normality test indicated that the data was not homogeneous, then a Mann Whitney test was used. To determine the relationship between the two treatment groups a statistical analysis paired t-test was used. If the normality test showed the data distribution was not homogeneous, then a Wilcoxon rank statistical test was used by applying SPSS version 17 (SPSS Inc). The difference of P<0.05 was declared significant.

Patients were treated for 3 months with a dose of 1 capsule, 3×/day as complementary therapy. Each capsule contained 250 mg polysaccharide, which contained 180 mg β-1,3/1,6-D-glucan. The specific composition of each dose is shown below in Table 5.

TABLE 5

| Component | Amount per capsule |
| --- | --- |
| Polysaccharides (Consist of glucose, galactose, arabinose, xylose, mannose and linked by β-glycosidic linkages) | 250 mg |
| β-D-Glucan content in Polysaccharide | 200 mg |
| β-1,3/1,6-D-Glucan content in β-D-Glucan | 180 mg |
| Protein | 10 mg |
| As | 0 ppm |
| Cd | <1.5 ppm |
| Pb | <9 ppm |

Summary of Data for Patients Having Stable Angina Pectoris (SAP)

FIGS. 6A-10 show data for pre- and post-administration of the β-1,3/1,6-D-glucan for subjects in the SAP group. Table 6 shows a summary of divergence test in the SAP group assays.

TABLE 6

| Variable | Mean | Sig (P) |
| --- | --- | --- |
| Pre IL-6 | 294.70 ± 123.28 | 0.000 |
| Post IL-6 | 24.41 ± 21.45 | |
| Pre TNF alpha | 11444 ± 2352.70 | 0.000 |
| Post TNF alpha | 476.13 ± 482.89 | |
| Pre CRP | 20158.88 ± 8968.08 | 0.000 |
| Post CRP | 2092 ± 1437.16 | |
| Pre MDA | 95.63 ± 21.27 | 0.000 |
| Post MDA | 44.84 ± 50.95 | |
| Pre SOD | 3.41 ± 0.46 | 0.001 |
| Post SOD | 5.97 ± 4.19 | |
| Pre Adiponectin | 33.33 ± 20.56 | 0.207 |
| Post Adiponectin | 21.65 ± 10.99 | |
| Pre Cholest | 205.49 ± 48.49 | 0.081 |
| Post Cholest | 182.11 ± 73.81 | |
| Pre HDL | 46.20 ± 12.53 | 0.000 |
| Post HDL | 34.51 ± 16.56 | |
| Pre LDL | 126.17 ± 36.87 | 0.268 |
| Post LDL | 116.17 ± 54.16 | |
| Pre TG | 122.37 ± 52.04 | 0.974 |
| Post TG | 122.83 ± 98.54 | |
| Pre GLUC | 22.88 ± 12.44 | 0.342 |
| Post GLUC | 7.47 ± 6.22 | |
| Pre HBA1C | 7.68 ± 5.81 | 0.009 |
| Post HBA1C | 1.91 ± 2.52 | |
| Pre CEC % Gated | 7.87 ± 6.72 | 0.075 |
| Post CEC % Gated | 2.03 ± 3.05 | |
| Pre CEC % Total | 2.52 ± 3.05 | 0.000 |
| Post CEC % Total | 0.71 ± 1.41 | |
| Pre EPC % Gated | 15.01 ± 8.39 | 0.000 |
| Post EPC % Gated | 5.43 ± 5.37 | |
| Pre EPC % Total | 5.16 ± 4.59 | 0.000 |
| Post EPC % Total | 1.19 ± 1.76 | |
| Pre NO % Gated | 22.68 ± 12.44 | 0.000 |
| Post NO % Gated | 7.47 ± 6.22 | |
| Pre NO % Total | 7.68 ± 5.81 | 0.000 |
| Post NO % Total | 1.91 ± 2.52 | |
| Pre Systolic | 118.43 ± 47.07 | 0.225 |
| Post Systolic | 106.71 ± 52.91 | |
| Pre Diastolic | 72.66 ± 28.55 | 0.268 |
| Post Diastolic | 67.43 ± 32.57 | |

The following inflammatory markers showed a significant decrease: pretest IL-6 from 294.70±123.28 to 24.41±21.45 with p: 0.00; pretest TNF-alpha from 11444±2352.70 to 476.13±482.99 p: 0.00; and pretest CRP from 20158.8±8 8968.0±8 1437.16 to 2092 with p: 0.00. This was in accordance with the results of the corresponding animal studies.

For MDA and SOD antioxidant markers, it was found that pretest of MDA level decreased from 95.63±21.27 to 44.84±50.95, and pretest of SOD level increased from 3.41±0.46 to 5.97±4.19, which is in accordance with the corresponding animal studies. The obtained pretest adiponectin marker showed a decrease from 33.33±20.56 to 21.65±10.99. The result of this decline was affected by risk factors of the patient. High Adiponectin level plays a role in the protective function of hyperglycemia and dyslipidemia. The lipid profile showed that total cholesterol level decreased significantly compared to other lipids. Pretest total cholesterol: from 205.49±48.49 to 182.11±73.81 p: 0:08. This is consistent with the results of the corresponding animal studies described above.

HbA1c level were lowered significantly even when the glucose level did not show significant reduction. Pre-test HbA1c level decreased from 7.68±5.81 to 1.91±2.52, with p=0.009, whereas pre-test glucose level decreased from 22.88±12.44 to 7.47±6.22, with p=0.342. CEC levels decreased from pretest results of 7.87±8.72 to 2.03±3.05, p=0.075, while the EPC, which is a biomarker for endothelial neovascularization and repair, did not significantly increase, (from 15.01 to 5.43, with p=0.000). Without being bound by theory, this is likely due to risk factors affecting the patients, including hypertension, smoking, dyslipidemia, and/or diabetes.

Blood pressure systolic and diastolic levels did not show a significant decrease. Pretest systolic blood pressure decreased from 118.43±47.07 to 108.71±52.91, with p=0.225 and pretest diastolic blood pressure decreased from 72.86±28.55 to 67.43±32.57 with p=0.269.

Summary of Data for High Risk Patients

FIGS. 11A-15 show data for pre- and post-administration of the β-1,3/1,6-D-glucan for subjects in the high risk group. Table 7 shows a summary of divergence test of the high risk group.

TABLE 7

| Variable | Mean | Sig (P) |
| --- | --- | --- |
| Pre IL-6 | 279.75 ± 120.76 | 0.000 |
| Post IL-6 | 29.32 ± 26.44 | |
| Pre TNF alpha | 13447.64 ± 2199.46 | 0.000 |
| Post TNF alpha | 544.85 ± 292.06 | |
| Pre CRP | 25329 ± 8662.10 | 0.000 |
| Post CRP | 2659 ± 69 | |
| Pre MDA | 114.13 ± 24.58 | 0.000 |
| Post MDA | 36.84 ± 26.39 | |
| Pre SOD | 3.12 ± 0.70 | 0.219 |
| Post SOD | 3.62 ± 4.26 | |
| Pre Adiponectin | 24.74 ± 2.45 | 0.946 |
| Post Adiponectin | 35.09 ± 30.60 | |
| Pre Cholest | 219.46 ± 49.49 | 0.193 |
| Post Cholest | 201.43 ± 81.63 | |
| Pre HDL | 52.03 ± 12.18 | 0.000 |
| Post HDL | 40.76 ± 19.31 | |
| Pre LDL | 132.24 ± 38.75 | 0.580 |
| Post LDL | 127.08 ± 54.19 | |
| Pre TG | 128.97 ± 62.13 | 0.201 |
| Post TG | 115.03 ± 63.80 | |
| Pre GLUC | 89.78 ± 16.51 | 0.172 |
| Post GLUC | 91.81 ± 40.06 | |
| Pre HBA1C | 5.86 ± 0.83 | 0.240 |
| Post HBA1C | 5.34 ± 1.86 | |
| Pre CEC % Gated | 6.96 ± 4.51 | 0.000 |
| Post CEC % Gated | 1.99 ± 1.52 | |
| Pre CEC % Total | 2.07 ± 1.54 | 0.000 |
| Post CEC % Total | 0.6457 ± 0.66 | |
| Pre EPC % Gated | 13.06 ± 8.05 | 0.000 |
| Post EPC % Gated | 1.72 ± 2.24 | |
| Pre EPC % Total | 3.28 ± 3.66 | 0.010 |
| Post EPC % Total | 1.72 ± 2.24 | |
| Pre NO % Gated | 20.03 ± 11.15 | 0.000 |
| Post NO % Gated | 6.61 ± 5.23 | |
| Pre NO % Total | 5.35 ± 4.54 | 0.002 |
| Post NO % Total | 2.36 ± 2.62 | |
| Pre Systolic | 130.14 ± 43.37 | 0.109 |
| Post Systolic | 116.24 ± 56.68 | |
| Pre Diastolic | 80 ± 25.74 | 0.102 |
| Post Diastolic | 73.24 ± 33.85 | |

The following inflammatory markers showed a significant decrease in post-test results compared to pre-test results: pre-test IL-6 from 279.75±120.76±26.44 to 29.32 with p: 0.000; pretest TNF-alpha from 13447.84±2199.46 to 544.85±292.06, with p: 0.000; and pretest CRP from 25329±8682.10 to 2659±89 with p: 0.000. This data corresponded to the results from the animal data described above. For MDA and SOD antioxidant markers it was found that pretest MDA level decreased from 114.13±24.56 to 36.84±28.39 and pretest SOD increased from 0.70±3.12 to 3.62±4.26. This data corresponded to the results from the animal data described above.

The pre-test adiponectin marker increased from 24.74±2.45 to 35.09±30.60. This increase in adiponectin corresponded with the theory that high adiponectin levels play a role in protecting the vascular endothelium, particularly from dyslipidemia that damages vascular endothelium. The lipid profiles showed that total cholesterol level decreased significantly compared to other lipids; pretest total cholesterol decreased from 219.46±49.49 to 201.43±81.63 with p: 0172. This data was consistent with the results obtained in the animal studies described above.

The HbA1c level decreased significantly even when the glucose level did not decrease significantly. Pretest HbA1c levels decreased from 5.86±0.83 to 5.34±1.88, with p=0.009, whereas pretest glucose level from 89.78±18.51 increased to 91.81±40.06, with p=0.342. Pretest CEC level decreased from 6.96±4.51 to 1.59±1.52, p=0.000, while EPC did not increase significantly: 13.06±8.05 to 1.72±2.24, with p=0.000. Without being bound by theory, this is likely due to risk factors affecting the patients, including hypertension, smoking, dyslipidemia, and/or diabetes.

Systolic and diastolic blood pressure levels did not show a significant decrease. Pre-test systolic blood pressure decreased from 130.14±43.37 to 118.24±55.68, with p=0.109 and pre-test diastolic blood pressure decreased from 80±25.74 to 73.24±33.85 with p=0.102.

The data described above shows β-1,3/1,6-D-glucan anti-inflammatory activity, anti-oxidant activity, anti-lipid activity, and anti-endothelial dysfunction activity towards patients categorized in the stable angina pectoris (SAP) and High Risk groups, and that β-1,3/1,6-D-glucan is able to act as secondary prevention for patients with SAP and primary preventive for high risk subjects.

Example 3. Treatment of STEMI Using β-1,3/1,6-D-Glucan

Figure 16:
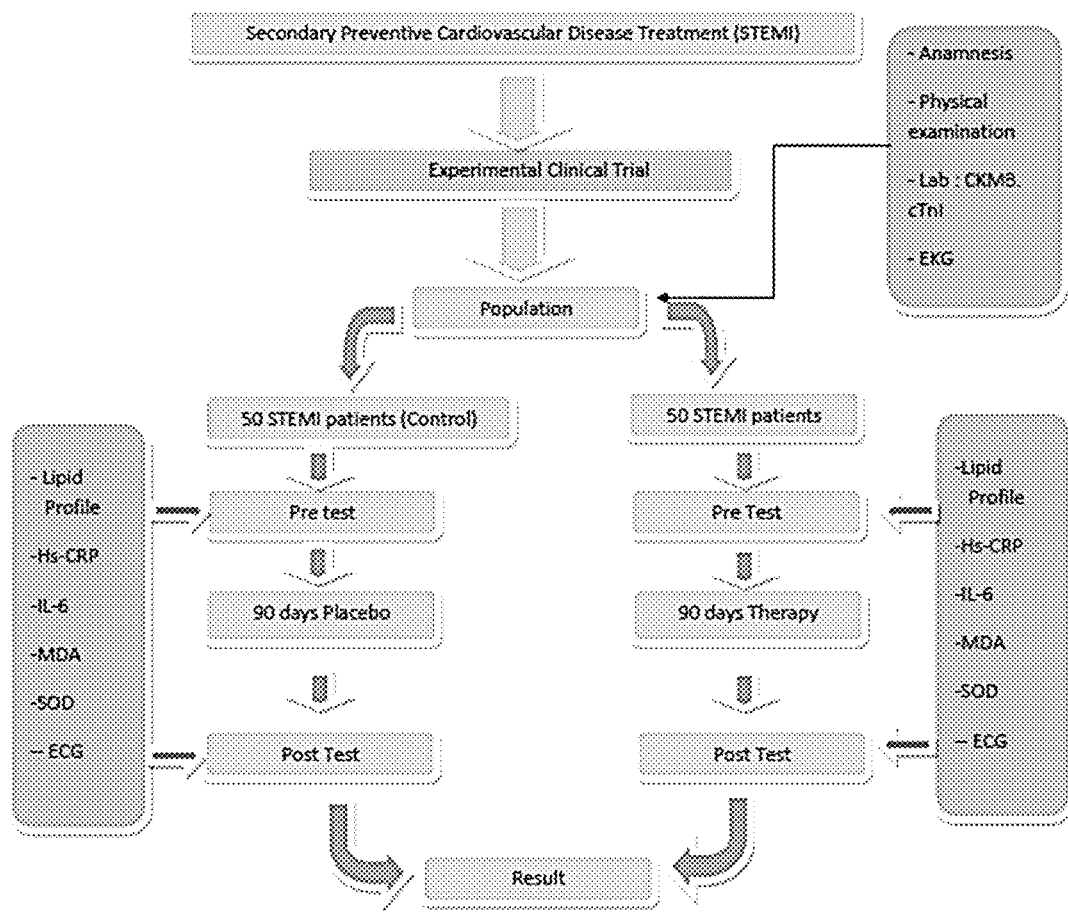
FIG. 16 shows a flow chart describing a treatment regimen of patients having STEMI by administration of β-1,3/1,6-D-glucan.

This study is an experimental clinical trial with human patients using perspective randomized control with pre- and post-test design of β-1,3/1,6-D-glucan administration for 90 days with a hypothesis based on results of the experiments described above in Example 2. The clinical trial is performed, for example, as shown in FIG. 16.

The targeted population is a representation of secondary prevention, a population with ST Elevation Myocardial Infarction with secondary prevention, i.e. Stable Angina Pectoris (criteria according to ESC 2014). STEMI is a clinical manifestation of atherosclerosis characterized by total occlusion of the coronary arteries that lead to unmet needs of oxygen in tissues. The treatment population will be divided into 2 groups, a control group and a treatment group. Both groups will receive different treatments (e.g., placebo for the control group and β-1,3/1,6-D-glucan for the treatment group) and a measurable significant difference is expected. The results will verify the results of studies described above in Example 2. The population that will receive β-1,3/1,6-D-glucan for 90 days will undergo patient stratification including physical examination, laboratory examination CKMB, cardio troponin I (cTnI), and ECG. Patients participating in the study will be given informed consent of the study.

The marker results to be studied are anti-inflammatory (Hs-CRP, IL-6), anti-oxidant (MDA and SOD) and lipid profile (TC, TG, HDL, LDL), analysis of LV function, LVEF, stroke volumes, LV mass index, fractional shortening, and wall segment analysis using echocardiograph that will be checked before the beginning of β-1,3/1,6-D-glucan administration and after the end of 90 days of administration of β-1,3/1,6-D-glucan. The obtained data will be analyzed statistically using SPSS 17:00.

Measurement of lipid profile, IL-6, hsCRP, MDA, and SOD in human blood is conducted through pre-test and post-test blood samples. Measurement of lipid profile (HDL, LDL, triglycerides and total cholesterol) is conducted through spectrophotometric colorimetric test using cobas-mira tool. Measurement of IL-1, TNF-α, IL-6, hsCRP, MDA, and SOD is performed using an ELISA kit.

Echocardiography is performed to assess LV function, LVEF, LV mass index, fractional shortening, and analytics wall segments.

Data is presented in the form of mean±SD. To compare the difference between the 2 groups of patients with STEMI who receives placebo and patients with STEMI who received β-1,3/1,6-D-glucan treatment, different pre-test and post-test tests are performed using paired t test. If the normality test indicates that the data are not homogeneous, the Mann Whitney will be applied. To determine the relationship between 2 groups using statistical paired t-test analysis, if the normality of data distribution test is not homogeneous, the Wilcoxon rank statistical test will be applied. Statistical calculations are done with SPSS version 17 (SPSS Inc). Differences P of <0.05 is declared as significant.

Example 4. Treatment of Inflammatory Bowel Disease Using β-1,3/1,6-D-glucan

Based on the pathogenesis of inflammatory bowel disease (IBD), β-1,3/1,6-D-glucan can be used as an immunomodulator as a complementary therapy. For example, the β-1,3/1,6-D-glucan will modulate the activity of immune cells, so that the inflammatory process can be suppressed. The β-1,3/1,6-D-glucan is able to bind to the receptors of immune cells, including:

a. Dectin-1
b. Toll-like Receptor 2/4
c. Scavenger Receptor
d. Lactosylceramide
e. Complement Receptor-3 (CR-3)
f. Langerin Receptor The results of the experiments described in Example 2 demonstrate that β-1,3/1,6-D-glucan has anti-inflammatory activity as evidenced by the decrease in inflammatory biomarkers (e.g., TNF-α and IL-6) compared to before the patients are administered with β-1,3/1,6-D-glucan. In the pathogenesis of IBD, the production of TNF-α and IL-6 occurs as a result of inflammatory processes; therefore, β-1,3/1,6-D-glucan would be beneficial as an anti-inflammation agent in treating IBD, either alone or in combination with other therapeutic agents. For example, β-1,3/1,6-D-glucan can be used as a complementary therapy for treating Ulcerative Colitis (UC) when combined with a standard therapy for treating UC, such as 5-ASA (5-aminosalicylic acid) and glisodin (enzyme superoxide dismutase/SOD). The addition of β-1,3/1,6-D-glucan in standard therapy provides improvements to the parameters observed. Upon administration of β-1,3/1,6-D-glucan to subjects having IBD, the following parameters will be measured: erythrocyte sedimentation rate, fecal calprotectin, fecal M2PK, and C-reactive protein. Additional examples of inflammatory parameters observed in UC are shown below in Table 8.

TABLE 8

| NO | Ulcerative Colitis Parameter Observed at One of International Studies (sumber: clinicaltrials.gov) | Ulcerative Colitis Parameter Observed by the Indonesian Medical Doctors |
| --- | --- | --- |
| 1. | C-Reactive Protein (CRP) | C-Reactive Protein (CRP) |
| 2. | Interleukin-2 (IL-2) | Erythrocyte sedimentation rate |
| 3. | Interleukin-6 (IL-6) | Stool Calprotectin |
| 4. | Tumor Necrosis Factor - α (TNF-α) | Stool M2-Pyruvate Kinase (M2-PK) |
| 5. | Stool Calprotectin | |
| 6. | Inflammatory Bowel Diseases Questionnaire (IBDQ) | |
| 7. | Subject Global Impression of Change (SGIC) | |
| 8. | Physician's Global Assessment of Illness Severity (PGAS) | |
| 9. | Ulcerative Colitis Symptoms: Pain | |
| 10. | Ulcerative Colitis Symptoms: Stool Frequency | |
| 11. | Ulcerative Colitis Symptoms: Rectal Bleeding | |
| 12. | Plasma Endocannabinoid Levels: 2-arachidonylglycerol (2-AG) | |
| 13. | Plasma Endocannabinoid Levels: anandamide (AEA) | |
| 14. | Plasma Endocannabinoid Levels: oleoylethanolamide (OEA) | |
| 15. | Clinical Body Weight Assessment | |

Example 5. Effect of β-1,3/1,6-D-Glucan on Hematologic Profile 80 rats were randomly divided into 4 groups of female rats and 4 groups of male rats (10 rats/group). The four groups of male and female rats were subdivided into 3 treatment groups that received β-1,3/1,6-D-glucan at a dose of 300, 600, and 1200 mg/kg body weight (BW)/day for 90 days; and 1 control group. The following hematologic profile parameters were measured after 90 days:

Leukocytes
Platelets
Erythrocytes
Plateletcrit (PCT)
Mean corpuscular volume (MCV)
Mean corpuscular hemoglobin (MCH)
Red cell distribution width (RDW)

One-way test of the analysis of variance test (ANOVA) showed that there was no significant difference in the value of leukocytes between the control group and the treatment group receiving 3 variants of the β-1,3/1,6-D-glucan dose. Significant differences occurred in the value of erythrocytes and platelets, PCT, MCV, MCH, and RDW levels between the control group and the three treatment groups, but the difference was still within the normal range. These data suggest that β-1,3/1,6-D-glucan with a dose of 300, 600, and 1200 mg/kg BW/day do not have a harmful effect on blood components (hematological profile).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating ST-elevation myocardial infarction in a subject in need thereof, comprising administering to the subject a therapeutically effective amount of β-1,3/1,6-D-glucan, or a pharmaceutically acceptable salt thereof, and one or more of additional therapeutic agents each independently selected from the group consisting of an angiotensin-converting enzyme inhibitor, an angiotensin II receptor blocker, a beta blocker, a diuretic, an aldosterone antagonist, and digoxin;
wherein the method further comprises identifying or having identified the subject as exhibiting abnormal expression of one or more cytokines, and wherein the therapeutically effective amount is obtained by measuring the expression changes of interleukin-6, tumor necrosis factor-α, and C-reactive protein between pre- and post-administration of the β-1,3/1,6-D-glucan.

2. A method of treating ST-elevation myocardial infarction in a subject in need thereof, comprising administering to the subject a therapeutically effective amount of a pharmaceutical composition comprising β-1,3/1,6-D-glucan, or a pharmaceutically acceptable salt thereof, and one or more pharmaceutically acceptable excipients, and one or more of additional therapeutic agents each independently selected from the group consisting of an angiotensin-converting enzyme inhibitor, an angiotensin II receptor blocker, a beta blocker, a diuretic, an aldosterone antagonist, and digoxin;
wherein the method further comprises identifying or having identified the subject as exhibiting abnormal expression of one or more cytokines, and wherein the therapeutically effective amount is obtained by measuring the expression changes of interleukin-6, tumor necrosis factor-α, and C-reactive protein between pre- and post-administration of the β-1,3/1,6-D-glucan.

3. The method of claim 1, wherein the subject is identified or has been identified as a subject exhibiting one or more symptoms of the ST-elevation myocardial infarction.

4. The method of claim 1, wherein the administering step comprises administering about 500 mg to about 600 mg β-1,3/1,6-D-glucan, or a pharmaceutically acceptable salt thereof, to the subject.

5. The method of claim 1, wherein the subject is identified or has been identified as exhibiting abnormal expression of interleukin-6, interleukin-10, tumor necrosis factor-α, C-reactive protein, or any combination thereof.

6. The method of claim 1, wherein the administering step comprises administering about 500 mg to about 550 mg β-1,3/1,6-D-glucan, or a pharmaceutically acceptable salt thereof, to the subject.

7. The method of claim 1, wherein the β-1,3/1,6-D-glucan, or a pharmaceutically acceptable salt thereof, has a molecular weight of from about 3600 kDa to about 4200 kDa.

8. The method of claim 2, wherein the pharmaceutical composition comprises about 500 mg to about 600 mg of the β-1,3/1,6-D-glucan, or a pharmaceutically acceptable salt thereof.

9. The method of claim 2, wherein the pharmaceutical composition comprises about 500 mg to about 550 mg of the β-1,3/1,6-D-glucan, or a pharmaceutically acceptable salt thereof.

10. The method of claim 2, wherein the β-1,3/1,6-D-glucan, or a pharmaceutically acceptable salt thereof, has a molecular weight of from about 3600 kDa to about 4200 kDa.

11. The method of claim 2, wherein the subject is identified or has been identified as exhibiting abnormal expression of interleukin-6, interleukin-10, tumor necrosis factor-α, C-reactive protein, or any combination thereof.

12. The method of claim 2, wherein the pharmaceutical composition comprises 100 mg to about 200 mg of the β-1,3/1,6-D-glucan.

13. The method of claim 2, wherein the pharmaceutical composition comprises about 180 mg of the β-1,3/1,6-D-glucan.

14. The method of claim 1, wherein the additional therapeutic agent is an angiotensin-converting enzyme inhibitor.

15. The method of claim 1, wherein the additional therapeutic agent is an angiotensin II receptor blocker.

16. The method of claim 1, wherein the additional therapeutic agent is a beta blocker.

17. The method of claim 1, wherein the additional therapeutic agent is a diuretic.

18. The method of claim 1, wherein the additional therapeutic agent is an aldosterone antagonist.

19. The method of claim 1, wherein the additional therapeutic agent is a digoxin.

20. The method of claim 2, wherein the additional therapeutic agent is an angiotensin-converting enzyme inhibitor.

21. The method of claim 2, wherein the additional therapeutic agent is an angiotensin II receptor blocker.

22. The method of claim 2, wherein the additional therapeutic agent is a beta blocker.

23. The method of claim 2, wherein the additional therapeutic agent is a diuretic.

24. The method of claim 2, wherein the additional therapeutic agent is an aldosterone antagonist.

25. The method of claim 2, wherein the additional therapeutic agent is a digoxin.

* * * * *